United States Patent
Sakai et al.

[11] Patent Number: 5,729,133
[45] Date of Patent: Mar. 17, 1998

[54] NONCONTACT TYPE MAGNETIC HEAD FOR DETECTING RATE-OF-WEAR IN A ROTATING MAGNETIC HEAD

[75] Inventors: Seiichi Sakai, Tokyo; Teruyuki Yoshida, Kanagawa, both of Japan

[73] Assignee: Sony Corporation, Tokyo, Japan

[21] Appl. No.: 708,853

[22] Filed: Sep. 9, 1996

[30] Foreign Application Priority Data

Sep. 13, 1995 [JP] Japan .................................. 7-235235

[51] Int. Cl.$^6$ .............. G11B 5/00; G01R 33/12; G01N 27/72
[52] U.S. Cl. .................. 324/237; 324/210; 360/137
[58] Field of Search .................. 324/210, 211, 324/212, 226, 229, 234, 236, 237, 238; 360/31, 84, 110, 119, 137

[56] References Cited

U.S. PATENT DOCUMENTS 3,938,193 2/1976 Sargunar .......................... 360/137

Primary Examiner—Walter E. Snow
Attorney, Agent, or Firm—Jay H. Maioli

[57] ABSTRACT

A magnetic sensor is disposed in an opposing relationship to a rotating magnetic head device with a magnetic head mounted thereon and placed in noncontact therewith so as to fall outside a lap angle α of a magnetic tape. The magnetic sensor is used as a part of oscillating elements of an oscillator circuit. By noting that a magnetic resistance of a magnetic circuit at a rotational position where the magnetic head faces the magnetic sensor changes according to the degree of extension of the magnetic head from the surface of a drum, and taking the change in magnetic resistance as a variation in oscillating frequency, the rate of wear of the magnetic head is measured. Since the change in magnetic resistance is taken as the variation in oscillating frequency, the degree of extension of the magnetic head, i.e., the rate of wear of the magnetic head can be measured with high accuracy. Since an apparatus for measuring the rate of wear of the magnetic head is a noncontact type, there is no risk that the magnetic head to be measured will be damaged. Owing to the above construction, the rate of wear of the magnetic head can be measured in the noncontact state and with high accuracy.

9 Claims, 20 Drawing Sheets

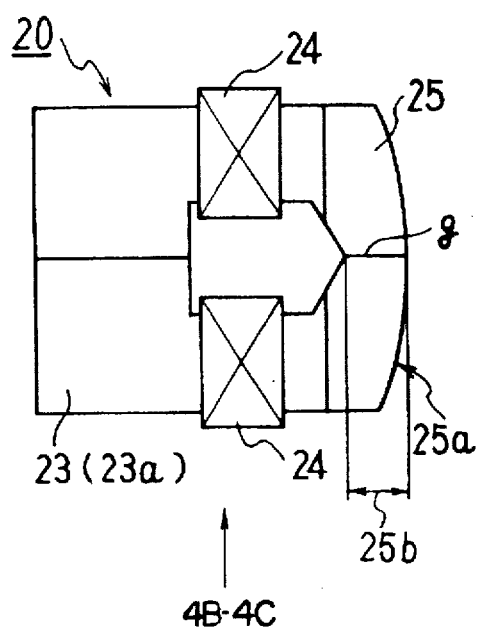
FIG. 4A
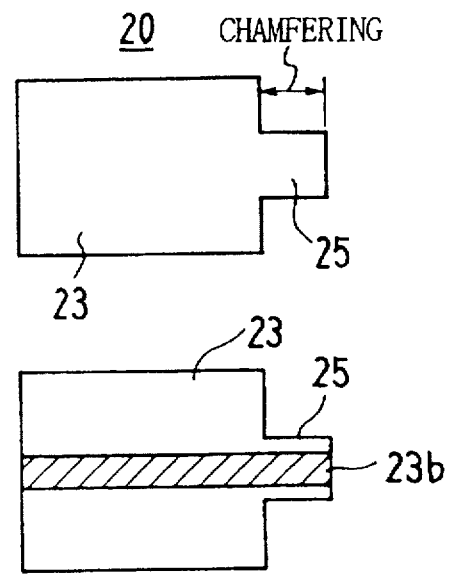
FIG. 4B
FIG. 4C
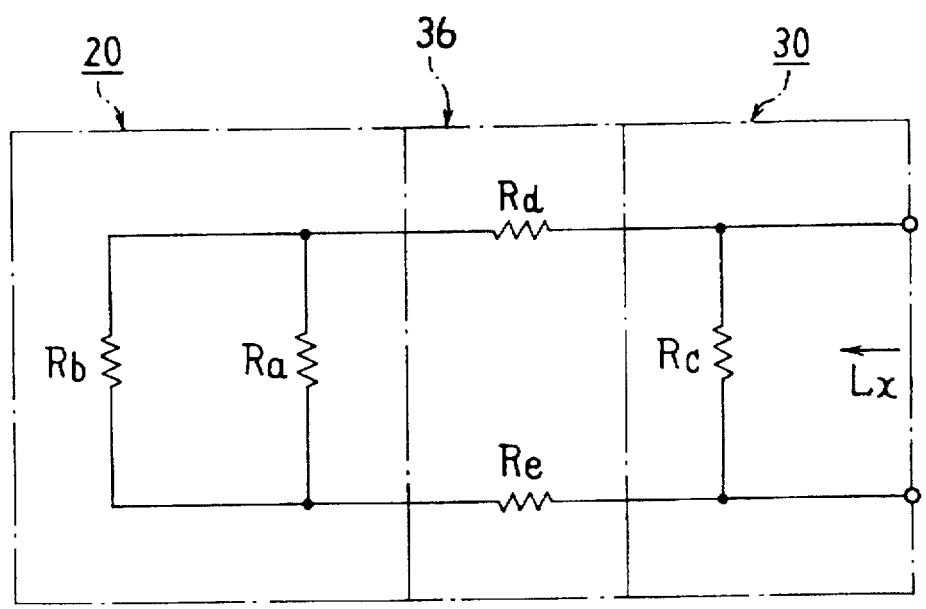
FIG. 5

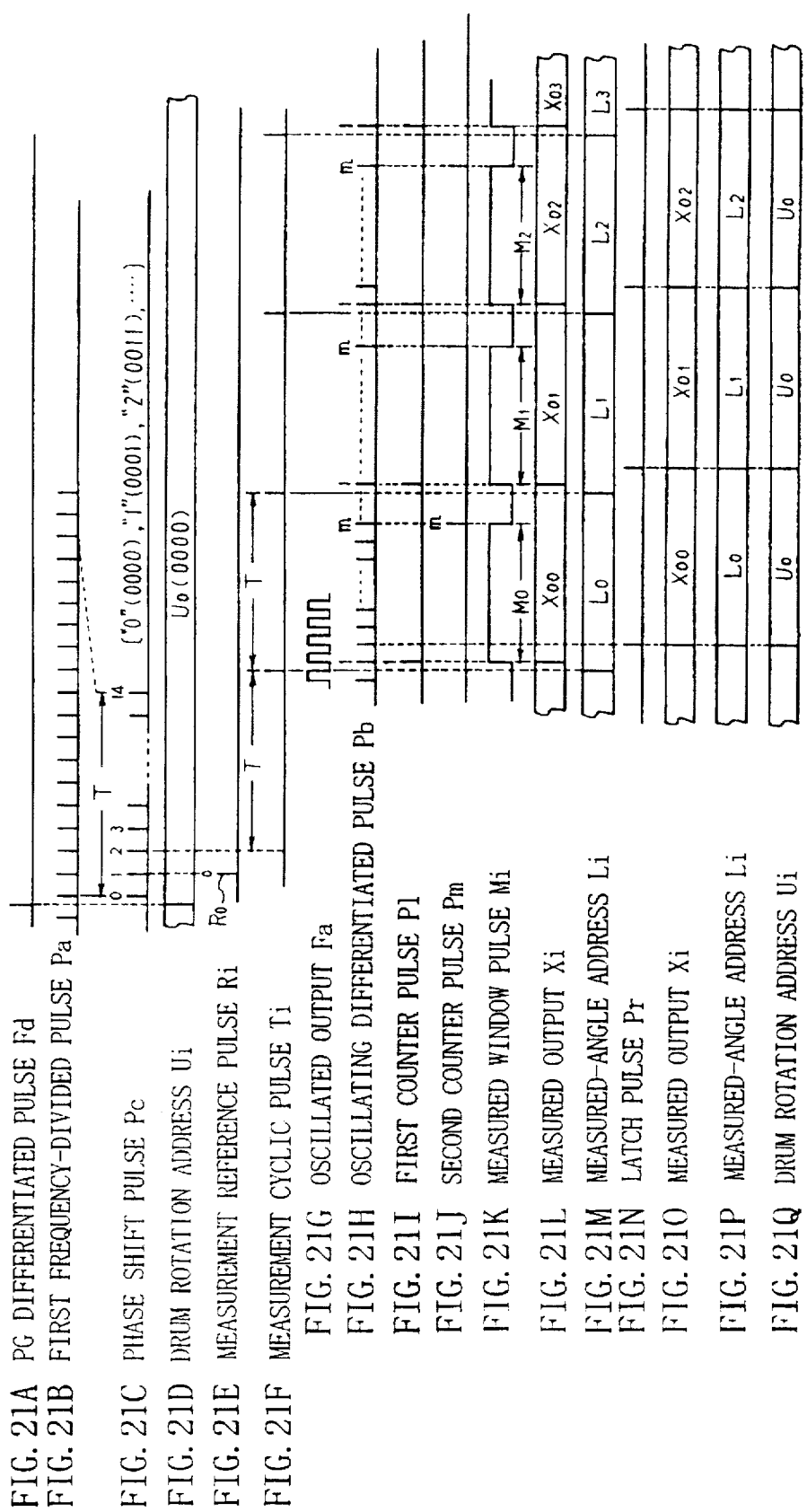

FIG. 21A PG DIFFERENTIATED PULSE Fd
FIG. 21B FIRST FREQUENCY-DIVIDED PULSE Pa

FIG. 21C PHASE SHIFT PULSE Pc
FIG. 21D DRUM ROTATION ADDRESS Ui
FIG. 21E MEASUREMENT REFERENCE PULSE Ri
FIG. 21F MEASUREMENT CYCLIC PULSE Ti
FIG. 21G OSCILLATED OUTPUT Fa
FIG. 21H OSCILLATING DIFFERENTIATED PULSE Pb
FIG. 21I FIRST COUNTER PULSE Pl
FIG. 21J SECOND COUNTER PULSE Pm
FIG. 21K MEASURED WINDOW PULSE Mi
FIG. 21L MEASURED OUTPUT Xi
FIG. 21M MEASURED-ANGLE ADDRESS Li
FIG. 21N LATCH PULSE Pr
FIG. 21O MEASURED OUTPUT Xi
FIG. 21P MEASURED-ANGLE ADDRESS Li
FIG. 21Q DRUM ROTATION ADDRESS Ui

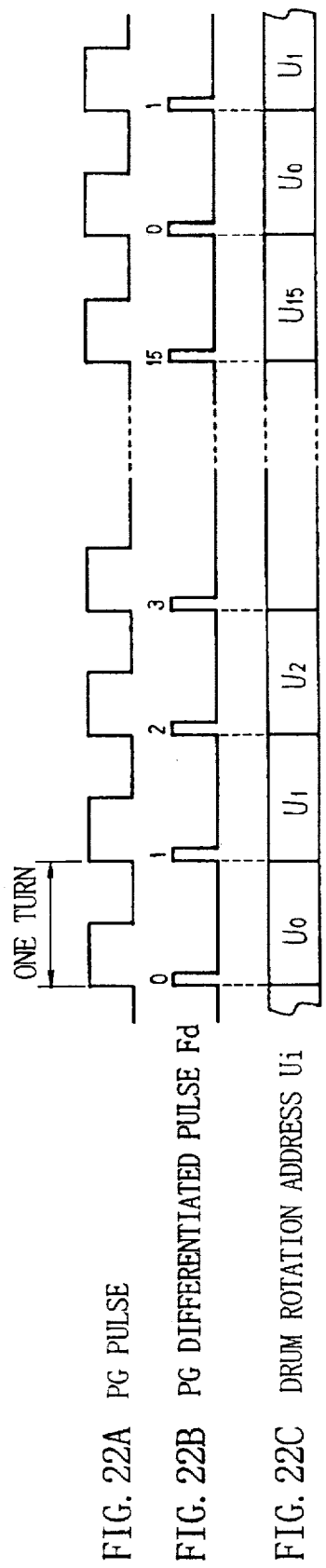
FIG. 22A PG PULSE
FIG. 22B PG DIFFERENTIATED PULSE Fd
FIG. 22C DRUM ROTATION ADDRESS Ui

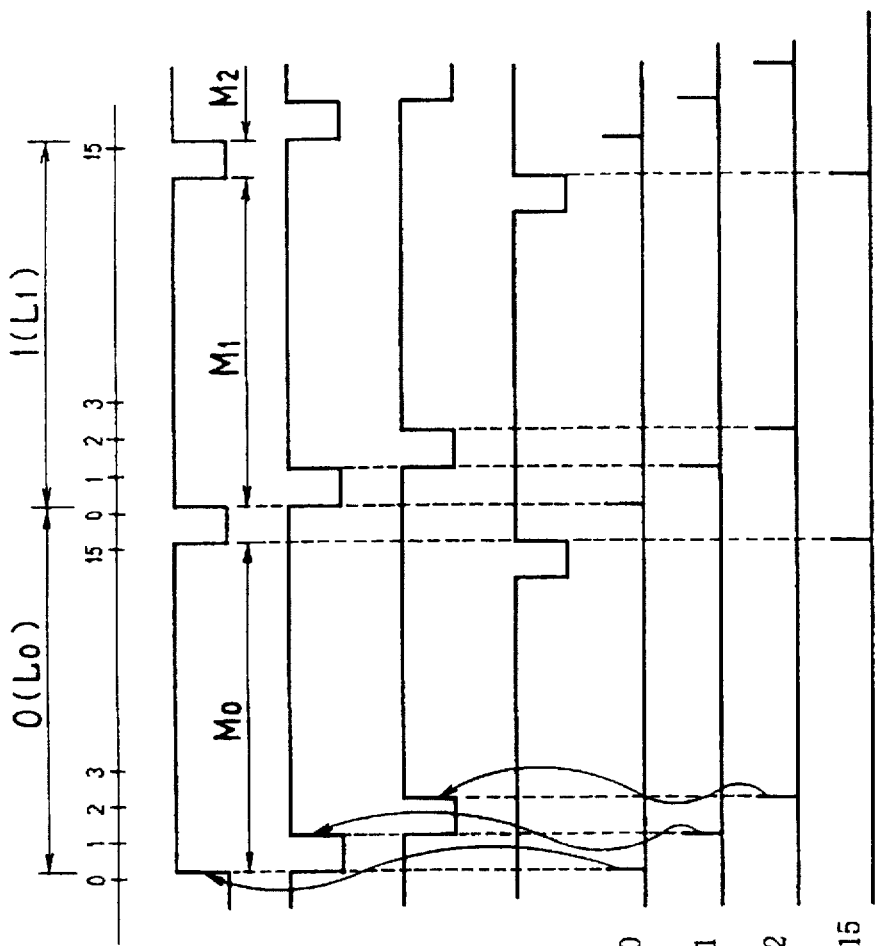
FIG. 24A MEASURED WINDOW PULSE Mi
FIG. 24B MEASURED WINDOW PULSE Mi
FIG. 24C MEASURED WINDOW PULSE Mi
FIG. 24D MEASURED WINDOW PULSE Mi
FIG. 24E MEASUREMENT REFERENCE PULSE R0
FIG. 24F MEASUREMENT REFERENCE PULSE R1
FIG. 24G MEASUREMENT REFERENCE PULSE R2
FIG. 24H MEASUREMENT REFERENCE PULSE R15

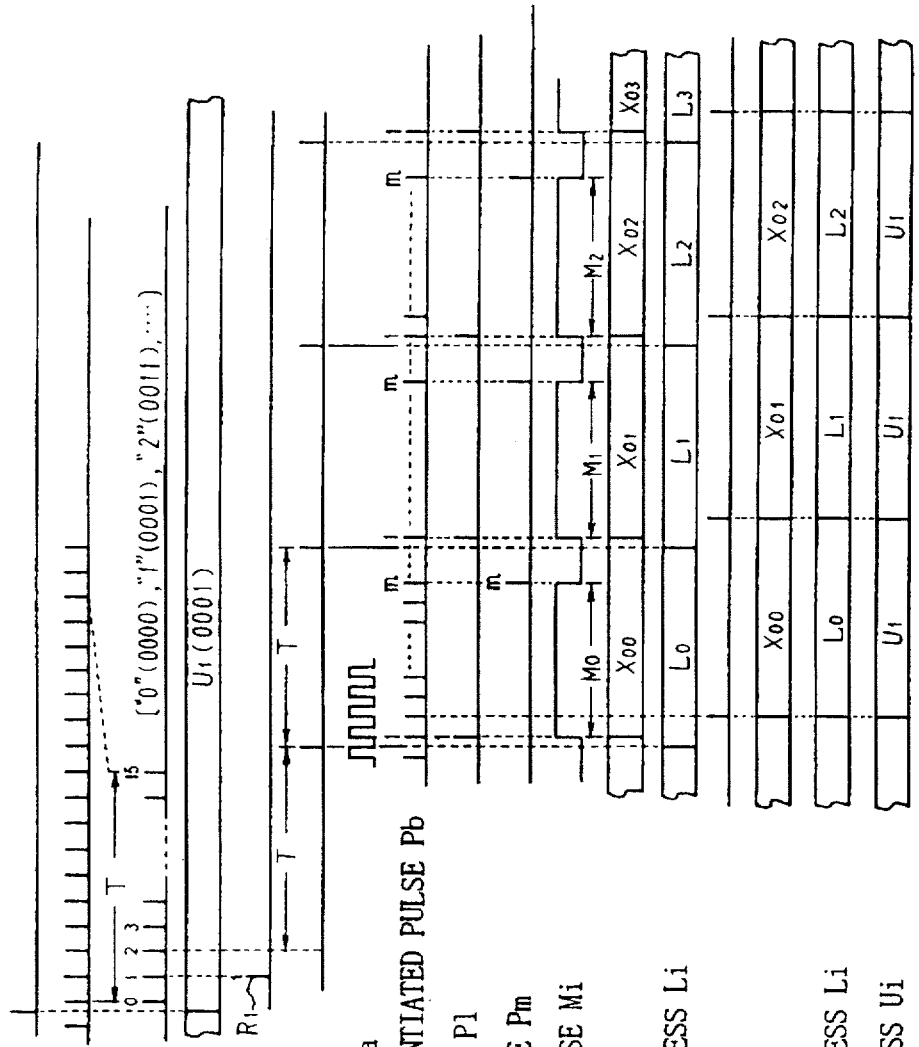

FIG. 25A PG DIFFERENTIATED PULSE Fd
FIG. 25B FIRST FREQUENCY-DIVIDE PULSE Pa
FIG. 25C PHASE SHIFT PULSE Pc
FIG. 25D DRUM ROTATION ADDRESS Ui
FIG. 25E MEASUREMENT REFERENCE PULSE Ri
FIG. 25F MEASUREMENT CYCLIC PULSE Ti
FIG. 25G OSCILLATED OUTPUT Fa
FIG. 25H OSCILLATING DIFFERENTIATED PULSE Pb
FIG. 25I FIRST COUNTER PULSE Pl
FIG. 25J SECOND COUNTER PULSE Pm
FIG. 25K MEASURED WINDOW PULSE Mi
FIG. 25L MEASURED OUTPUT Xi
FIG. 25M MEASURED-ANGLE ADDRESS Li
FIG. 25N LATCH PULSE Pr
FIG. 25O MEASURED OUTPUT Xi
FIG. 25P MEASURED-ANGLE ADDRESS Li
FIG. 25Q DRUM ROTATION ADDRESS Ui

NONCONTACT TYPE MAGNETIC HEAD FOR DETECTING RATE-OF-WEAR IN A ROTATING MAGNETIC HEAD

BACKGROUND OF THE INVENTION

1. Field of the Invention

This invention relates to a noncontact type magnetic head wear-rate measuring apparatus suitable for use in a rotating drum device using a magnetic head, such as a video tape recorder or the like. More specifically, the present invention relates to a noncontact type magnetic head wear-rate measuring apparatus wherein a magnetic sensor is disposed in noncontact with a rotating magnetic head device and the rate of wear of a magnetic head can be measured in a noncontact state and with high accuracy according to a variation in the total magnetic resistance between the magnetic head and the magnetic sensor.

2. Description of the Related Art

In AV devices each using a rotating drum device with a magnetic head mounted thereon, such as a video tape recorder (VTR), a data recorder, a digital audio tape recorder (DAT), etc., the magnetic head is driven in a state of being in contact with the magnetic tape. Therefore, a tape sliding portion of the magnetic head wears out due to the running of the magnetic tape over a long period of time.

When the rate of wear thereof reaches several tens of microns, a region (head depth) for forming a magnetic head gap disappears in the case of a normal magnetic head. Therefore, there may be cases in which when the magnetic head wears until the instance preceding the complete disappearance of the head depth, such a magnetic head interferes with recording and reproduction. Further, when the head sliding portion is used until the head depth completely disappears, the worst case occurs and hence a signal cannot be recorded and reproduced.

Since, in this case, a signal reproduced from the magnetic tape is brought to zero when the rate of wear of the head has reached several tens of microns during signal reproduction, a malfunction in the magnetic head can be immediately recognized.

However, when the rate of wear of the head has reached several tens of microns during recording of a signal, there is the risk that the signal cannot be normally recorded and important information is excluded from its record. This abnormal condition cannot be confirmed unless the recorded signal is reproduced. Thus, when the AV devices are used in particular for commercial use, such a situation must be avoided.

Therefore, particularly when the rate of wear of the head employed in each AV device for commercial use is monitored and the rate of wear of the head reaches a predetermined value, the AV device preferably warns a user of this fact so as to urge the user to perform its maintenance and inspection. It is therefore necessary to measure the rate of wear of the head. In this case, however, a contact type measuring apparatus or a noncontact type measuring apparatus is considered as this type of measuring apparatus.

In the contact type magnetic head wear-rate measuring apparatus, a measuring jig such as a measuring element or probe is mounted to a magnetic head to be measured so as to come into contact with the magnetic head. Therefore, there is the possibility that a tape sliding surface of the magnetic head to be measured has flaws or the magnetic head will break in the worst case. The result of measurements varies depending on how the measuring probe is mounted to the magnetic head and an influence exerted on measuring accuracy cannot be overlooked.

When the rate of wear of a magnetic head to be measured is measured by the noncontact type magnetic head wear-rate measuring apparatus, the present measuring apparatus does not cause such a problem as produced in the contact type magnetic head wear-rate measuring apparatus. The noncontact type magnetic head wear-rate measuring apparatus measures the rate of wear of the head using light. In this case, a laser beam or the like is used as the light. Since the laser beam must be focused onto a tape sliding surface of the magnetic head so as to be accurately applied onto the tape sliding surface, the layout, adjustments and the like of a laser optical system become so troublesome. The measuring apparatus itself increases in volume due to the use of the optical system and a manufacturer gets very nervous at the assembly of the measuring apparatus into the rotating drum device.

SUMMARY OF THE INVENTION

With the foregoing problems in view, it is an object of the present invention to provide a noncontact type magnetic head wear-rate measuring apparatus capable of measuring the rate of wear of a magnetic head in a noncontact state and measuring the rate of head wear with high accuracy.

According to one aspect of the present invention, for achieving the above object, there is provided a noncontact type magnetic head wear-rate measuring apparatus, comprising:

a magnetic sensor opposed to a rotating magnetic head device with a magnetic head mounted thereon and disposed in a state placed in noncontact with the rotating magnetic head device so as to fall outside from an angle at which a magnetic tape is wound around the rotating magnetic head device; and means for calculating the rate of wear of the magnetic head in response to an output produced from the magnetic sensor; and wherein the magnetic sensor serves as a part of a variable oscillator circuit element and the rate-of-wear calculating means measures the rate of wear of the magnetic head according to a variation in oscillating frequency of the magnetic sensor at a position of rotation of the rotating magnetic head device, where the magnetic sensor is opposed to the magnetic head.

The magnetic sensor is disposed at and fixed to a position which falls outside a tape lap angle. The magnetic sensor comprises an inverted U-shaped frame core and a detecting coil wound in a winding groove defined in the core. The width of the winding groove is wider than a gap width of the magnetic head and is narrower than the width of the magnetic head.

Since the total value of magnetic resistance including a plurality of magnetic heads and a magnetic sensor at rotational positions where the magnetic heads are respectively opposed to the magnetic sensor, changes as the magnetic heads wear out, a variation in magnetic resistance is taken as a variation in inductance. Since the inductance is a part of oscillator circuit elements, the oscillating frequency thereof also changes with the variation in inductance. Since the rate of wear of each magnetic head and the change in oscillating frequency are correlated with each other, an oscillating frequency at the time the rate of head wear is zero, is stored. If a variation in the subsequent oscillating frequency is monitored, then the rate of head wear at the time of its measurement can be recognized. When the rate of wear of the head exceeds a predetermined wear rate (predetermined value), a warning is issued to a user. This can avoid beforehand an undesired state that a signal is not suddenly recorded during recording of the signal.

The position of rotation of each magnetic head opposed to the magnetic sensor is detected based on a reference signal indicative of a rotational position reference of the rotating magnetic head device. When the plurality of magnetic heads are provided with steplike offsets defined relative to each other in the direction of rotation of the rotating magnetic head device, the size (thickness) of the magnetic sensor is selected so that a single magnetic sensor can cover the magnetic heads, i.e., the plurality of magnetic heads are all included within a magnetic gap of the magnetic sensor.

The above and other objects, features and advantages of the present invention will become apparent from the following description and the appended claims, taken in conjunction with the accompanying drawings in which preferred embodiments of the present invention are shown by way of illustrative example.

BRIEF DESCRIPTION OF THE DRAWINGS

While the specification concludes with claims particularly pointing out and distinctly claiming the subject matter which is regarded as the invention, it is believed that the invention, the objects, features and advantages thereof will be better understood from the following description taken in connection with the accompanying drawings in which:

FIGS. 4A, 4B, and 4C are views depicting the structure of a magnetic head to be measured;

FIG. 5 is an equivalent magnetic circuit diagram including a magnetic head and a magnetic sensor;

FIGS. 21A–21Q is a waveform chart for explaining the operation of the digital measuring circuit shown in FIG. 20;

FIGS. 22A–22C is a waveform chart showing an example of generation of drum addresses;

FIGS. 24A–24H is a diagram showing operating waveforms for providing high resolution based on a phase shift; and FIGS. 25A–25Q is a waveform chart for describing digital measurements.

DETAILED DESCRIPTION OF THE PREFERRED EMBODIMENTS

One embodiment of a noncontact type magnetic head wear-rate measuring apparatus according to the present invention, which is applied to a rotating drum device mounted to the above-described VTR, will hereinafter be described in detail with reference to the accompanying drawings.

Figure 1:
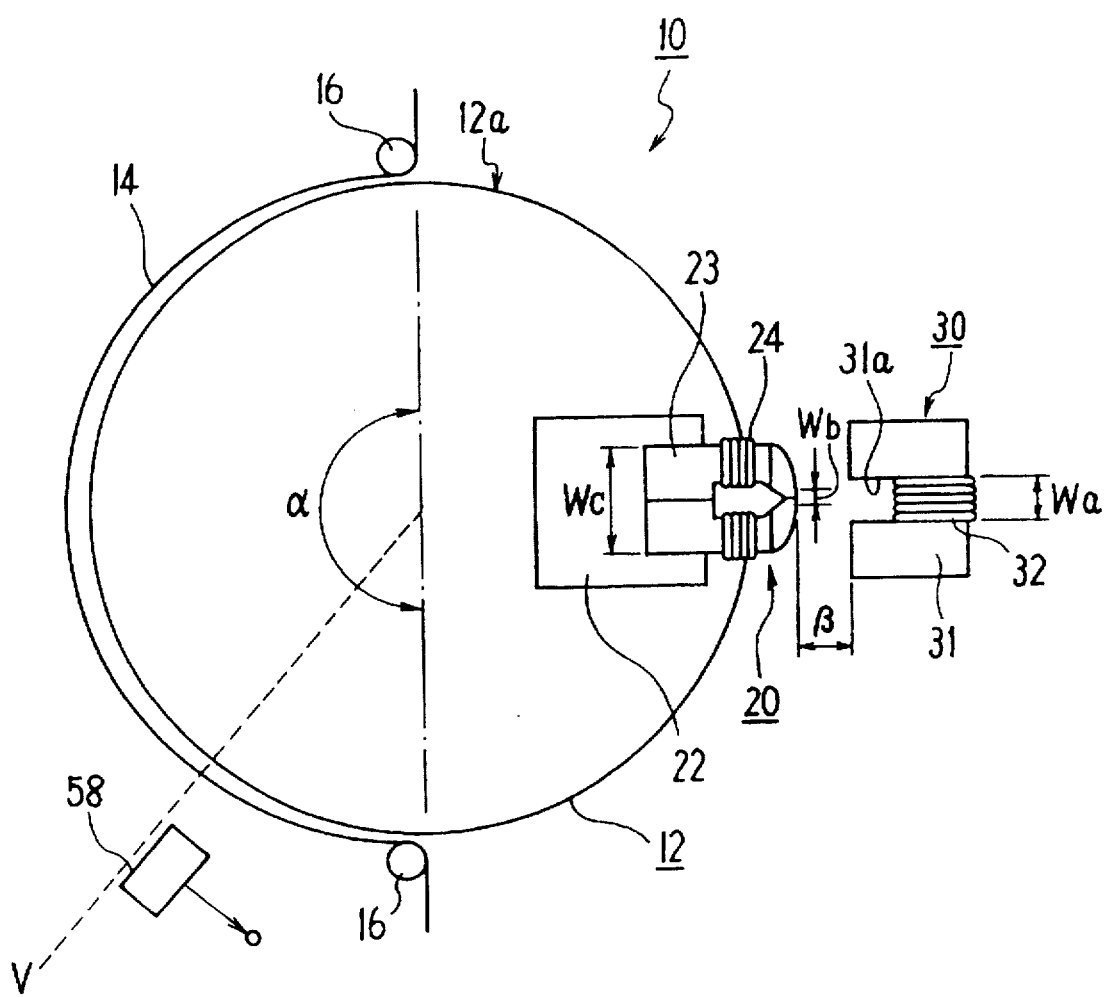
FIG. 1 is a conceptual view showing a summary of a noncontact type magnetic head wear-rate measuring apparatus according to the present invention.

FIG. 1 is a plan conceptual view showing a noncontact type magnetic head wear-rate measuring apparatus 10 to which the present invention is applied. In a rotating magnetic head device 12, a magnetic tape 14 is helically wound around a rotating drum (not shown) at a predetermined lap angle $\alpha$ defined by guide pins 16. Further, information is recorded on the magnetic tape 14 by a magnetic head 20 mounted to the rotating magnetic head device 12 and is reproduced or played back by the magnetic head 20.

A base 22 is placed in a predetermined position of the rotating magnetic head device 12. The magnetic head 20 is placed on and fixed to the base 22. The magnetic head 20 is mounted to the base 22 in a state of being projected from the surface of the rotating drum by a predetermined value or length. Signal windings 24 are respectively wound around both legs of a head core 23.

A magnetic sensor 30 is disposed in a position which is spaced a predetermined clearance $\beta$ from a drum surface 12a of the rotating magnetic head device 12, specifically, a sliding surface of the magnetic head 20 and which does not fall within the tape lap angle $\alpha$, e.g., an angular position away by 90° from the guide pins 16 when the lap angle $\alpha$ is about 180° as shown in the drawing. The magnetic sensor 30 comprises an inverted U-shaped frame core 31 and a detecting coil 32 wound in a winding groove 31a defined in the core 31. The detecting coil 32 wound around the magnetic sensor 30 serves as a part of oscillating elements of a variable oscillator circuit (OSC) to be described later.

Figure 2:
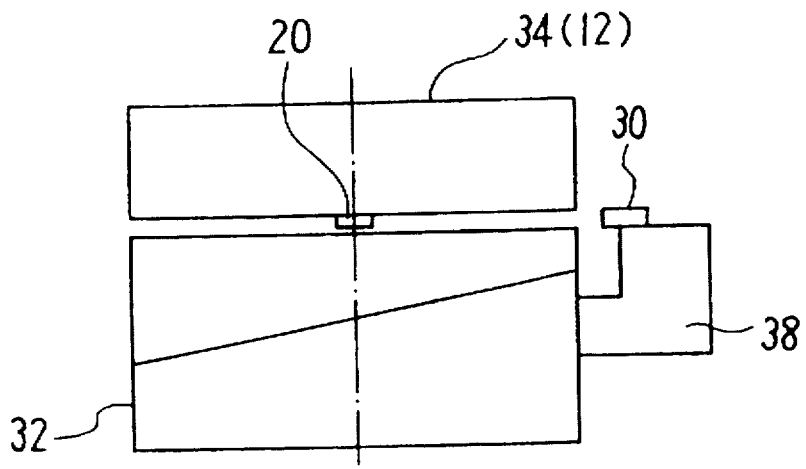
FIG. 2 is a configurational view illustrating one example of a rotating magnetic head device.
Figure 3:
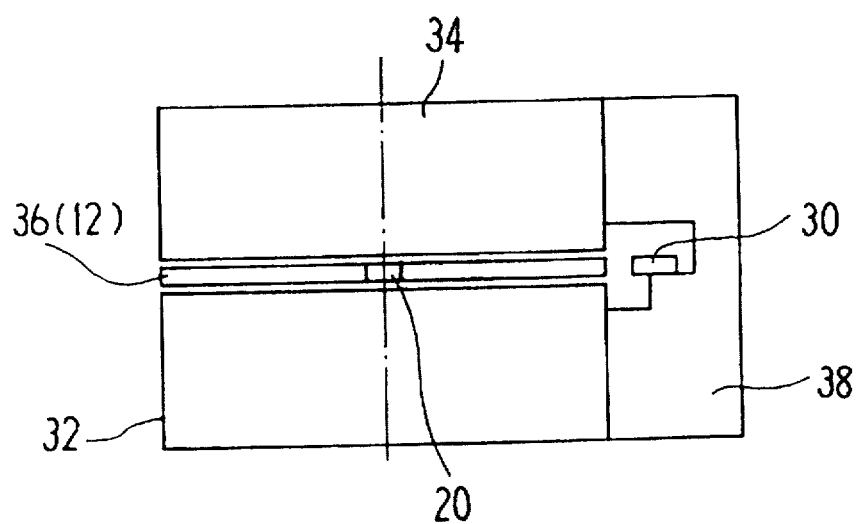
FIG. 3 is a configurational view showing another example of the rotating magnetic head device.

When the rotating drum device is constructed such that a lower drum 32 thereof is fixed and only an upper drum 34 is rotated as shown in FIG. 2, the upper drum 34 also functions as the rotating magnetic head device 12. At this time, the above-described magnetic sensor 30 is mounted and fixed to a mounting member 38 having an L-shaped cross section, which is attached to the lower drum 32, so as to be opposed to the magnetic head 20 of the upper drum 34.

On the other hand, when a rotating drum device having an intermediate drum (rotating drum) 36 and constructed such that a magnetic head 20 is mounted to the intermediate drum 36 and upper and lower drums 32 and 34 thereof are fixed to the intermediate drum 36, is used, a magnetic sensor 30 is mounted and fixed to an inverted U-shaped mounting member 38 provided across the upper and lower drums 32 and 34.

The magnetic head 20 is composed of a pair of cores 23 and signal windings 24 as shown in FIG. 4A. FIGS. 4B and 4C are respectively elevational views as seen from the direction indicated by arrow 4B–4C in the plan view of FIG. 4A. A tape sliding portion 25 including a tape sliding surface 25a is configured in a cut-away form as shown in FIG. 4B. Each of the cores 23 may be a single-layered core composed of only a magnetic substance or material as illustrated in FIG. 4B. Alternately, the core 23 may be a layered core in which a metal 23b is placed at the intermediate portion and non-magnetic materials (ceramic) are placed in positions above and below the metal 23b as shown in FIG. 4C.

Since the magnetic head 20 is rotating, two states: one in which the magnetic head 20 is in an opposing relationship to the magnetic sensor 30 during one turn or rotation and the other in which the magnetic head 20 is in an non-opposing relationship to the magnetic sensor 30, are produced. When the magnetic head 20 is in a state of being opposed to the magnetic sensor 30 as shown in FIG. 1, a magnetic circuit composed of the magnetic head 20 and the magnetic sensor 30 can be represented in the form of an equivalent circuit shown in FIG. 5.

In the equivalent circuit illustrated in FIG. 5, symbol Ra indicates a magnetic resistance of the tape sliding portion 25 and symbol Rb indicates a magnetic resistance of a back core (core 23 other than the head sliding portion 25). Similarly, the resistance of the detecting coil 32 of the magnetic sensor 30 is designated at symbol Rc. Further, magnetic resistance in a magnetic gap 36 at the time that the two are opposed to each other, are respectively represented as Rd and Re. Here, the magnetic resistance Rd and Re respectively correspond to magnetic resistance between both legs of the inverted U-shaped frame core 31 and the tape sliding portion 25.

Since the thickness of the tape sliding portion 25 decreases when the tape sliding portion 25 wears out, the magnetic resistance Ra changes. Simultaneously, since the opposed space or clearance between the tape sliding portion 25 and the magnetic sensor 30 also changes, the magnetic resistance Rd and Re also vary correspondingly. Thus, the total value of the magnetic resistance as viewed toward the magnetic head 20 from the magnetic sensor 30, is changed due to the wearing away of the magnetic head 20.

Figure 6:
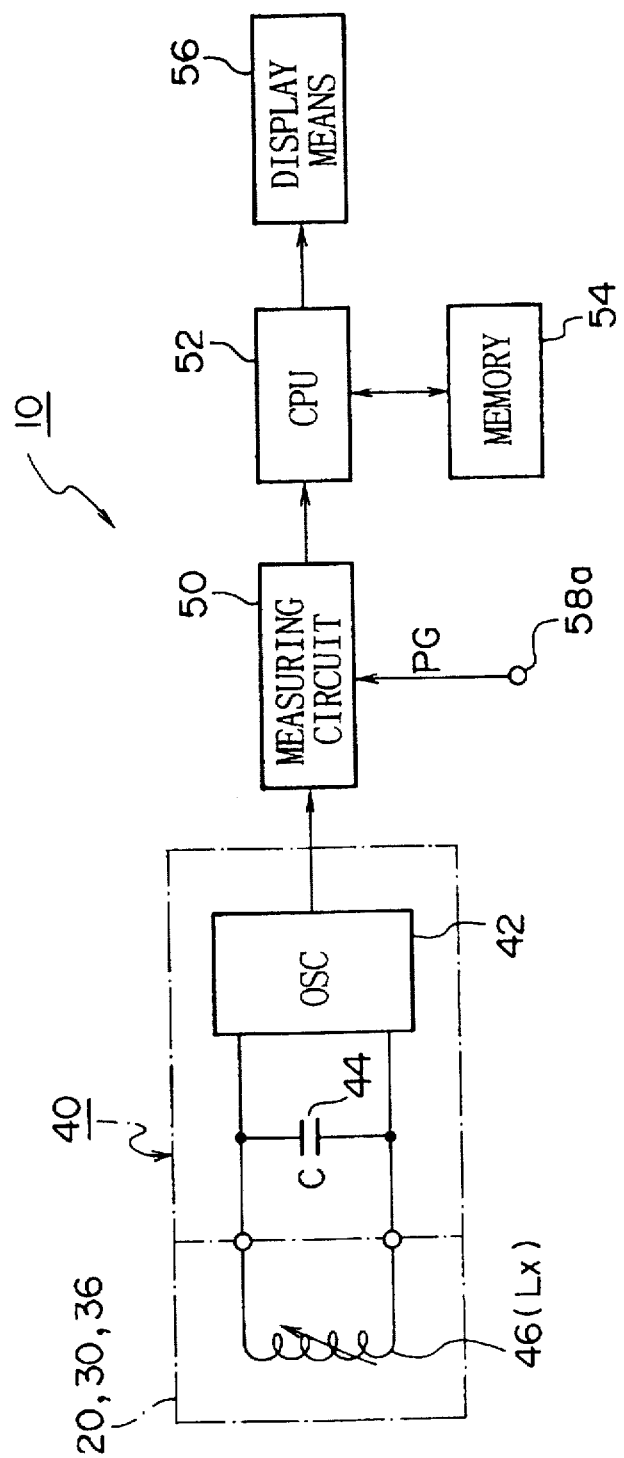
FIG. 6 is a systematic diagram showing one embodiment of a noncontact type magnetic head wear-rate measuring apparatus according to the present invention.

FIG. 6 is a view showing the summary of a circuit system of a noncontact type magnetic head wear-rate measuring apparatus 10 according to the present invention. A change in inductance due to the variation in magnetic resistance shown in FIG. 5 is introduced into a variable oscillator circuit 40. The variable oscillator circuit 40 has an amplifying stage 42 composed of transistors corresponding to amplifying elements for oscillation. In the present embodiment, LC elements are electrically connected to a parallel feedback path corresponding to the amplifying stage 42 as oscillating elements. The LC elements are a capacitor 44 corresponding to a capacitative element and a variable inductance element 46 electrically connected in parallel to the capacitor 44. The variable inductance element 46 indicates the total inductance Lx shown in FIG. 5.

When the inductance Lx varies, the oscillating frequency changes correspondingly. The oscillated output is introduced into a measuring circuit 50 where it is converted into a level (e.g., a voltage level) proportional to the frequency. For example, the oscillating frequency is counted by a counter and the oscillated output is converted into a voltage determined according to the count value thereof. Data measured in proportion to the oscillating frequency is supplied to a wear-rate calculating means 52 provided at a subsequent stage.

A CPU is provided within the wear-rate calculating means 52 and calculates the depth or rate of wear of the magnetic head 20 based on the resultant measured data. Data about the calculated wear rate or the like is stored in a memory 54 and supplied to a display means 56 to display the calculated value or the like thereon.

When the wear rate has reached a predetermined value or more, a notifying means (not shown) such as a warning means or the like may be activated aside from this process to inform a user that there is a possibility that information cannot be recorded properly if such a head is left as it is and the head must be immediately replaced by another. The predetermined value can be selected to a value immediately before, for example, a head depth (see 25b in FIG. 4A) vanishes or disappears. When the head depth is about 25μ, for example, 20μ or so can be selected as the predetermined value.

The above-described measuring process can be performed immediately after the power for the measuring apparatus has been turned on, for example. It has been understood from practical experience that when the magnetic head is normally used over a period of 500 to 1000 hours, it wears to several tens of microns, thus resulting in interference with recording and reproduction. Therefore, software may be constructed so that the measuring process is executed from the time immediately before such service time with the service time as a guide. The value of a recording current is controlled so as to be reduced with an increase in wear rate, aside from the measuring process and a magnetic head may be replaced by another only when the limit wear rate (corresponding to a value near the head depth) is detected.

The rate of head wear can be measured over the entire periphery of the drum. Alternatively, the wear rate may be measured only during a section or interval in which the magnetic head 20 and the magnetic sensor 30 confront each other. As shown in FIG. 1, a revolution detecting means (such as a pulse generator PG) 58 is provided on a direct extension of a radius which passes through the center of rotation of the drum. An angular position of rotation of the drum is detected on the basis of one PG pulse per turn or revolution of the drum, which is obtained from the revolution detecting means. Further, since the timing provided to measure the wear rate of the magnetic head by the magnetic sensor is determined, either of the above-described measurements can be made. This is because the relationship between the timing provided to obtain the PG pulse and the position of mounting of the magnetic head 20 to the drum is known and the relative positional relationship between the two is apparent in advance.

As shown in FIG. 1, a width Wa of the winding groove 31a defined in the core 31 that constitutes the aforementioned magnetic sensor 30, is selected so as to be greater than a width Wb of a gap g of the magnetic head 20 and narrower than a width Wc of the magnetic head 20 itself. This is made to create a magnetic gap between the magnetic sensor 30 and the magnetic head 20 as mentioned above and to change the value of each of the magnetic resistance formed by the magnetic head 20 and the magnetic sensor 30 according to the wear of the sliding surface 25a of the magnetic head 20. Examples of specific values of these will be mentioned as follows:

$$Wa=250 \mu m, Wb=0.5 \mu m \text{ and } Wc=1.5 mm$$

This is because when the width Wa of the winding groove 31a is narrower than the width Wb of the gap g of the magnetic head 20 (such a configuration is impossible in practice) and is broader than the width Wc of the magnetic head 20 itself, the rate of wear of the magnetic head 20 cannot be accurately taken as a change in magnetic resistance. Since the opposite clearance β exerts an influence on detection sensitivity, the optimum clearance value is selected.

When the magnetic sensor 30 is used and the wear rate of the head is measured according to the change in magnetic resistance thereof as in the present invention, a high-accuracy wear rate measurement can be realized by simply making a fine adjustment to the mounting position of the head so that the opposite clearance β is set according to the designed value. According to experiments, it has been confirmed that the head wear rate can be measured (and predicted) with an accuracy of ±1 μm. It has also been confirmed that in the case of a magnetic head using a layered core in particular, the rate of wear of the magnetic head can be measured with an accuracy of ±0 μm. Since the magnetic sensor 30 itself is a microminiaturized element and the other parts are circuit parts, the scale of the measuring apparatus becomes very small.

The magnetic head 20 mounted to the rotating magnetic head device 12 shown in FIG. 1 is illustrated as a single device for convenience of illustration. It is a general rule that several magnetic heads 20 are disposed with specific intervals held with respect to the direction of rotation thereof. Thus, even if the rate of wear of each head is measured in the case of the provision of the plurality of magnetic heads, the usage of a single magnetic sensor as the magnetic sensor would be wiser from the viewpoint of measuring accuracy and construction.

Figure 7:
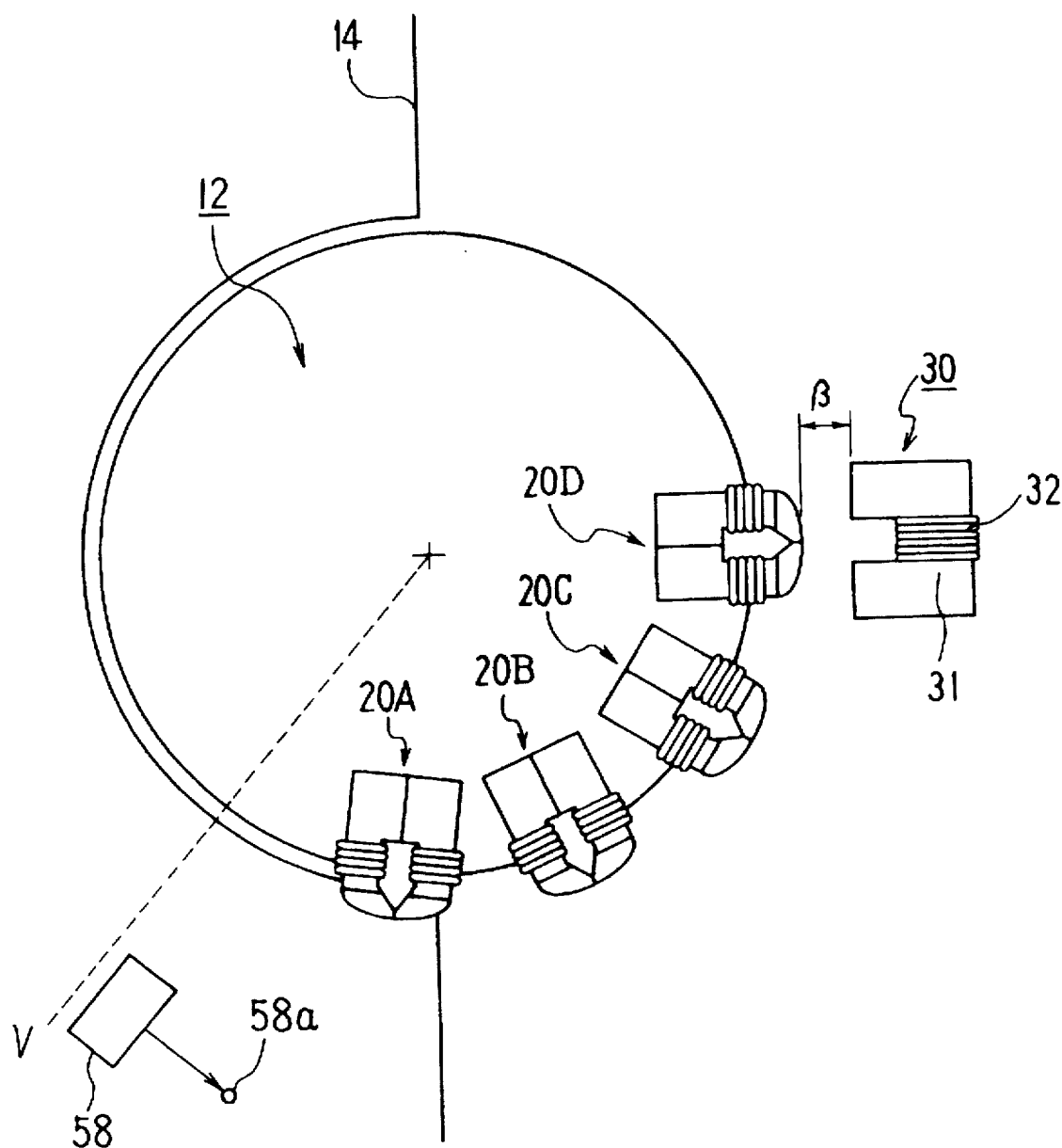
FIG. 7 is a view showing the same concept as that shown in FIG. 1 at a time that a plurality of magnetic heads are used.
Figure 8:
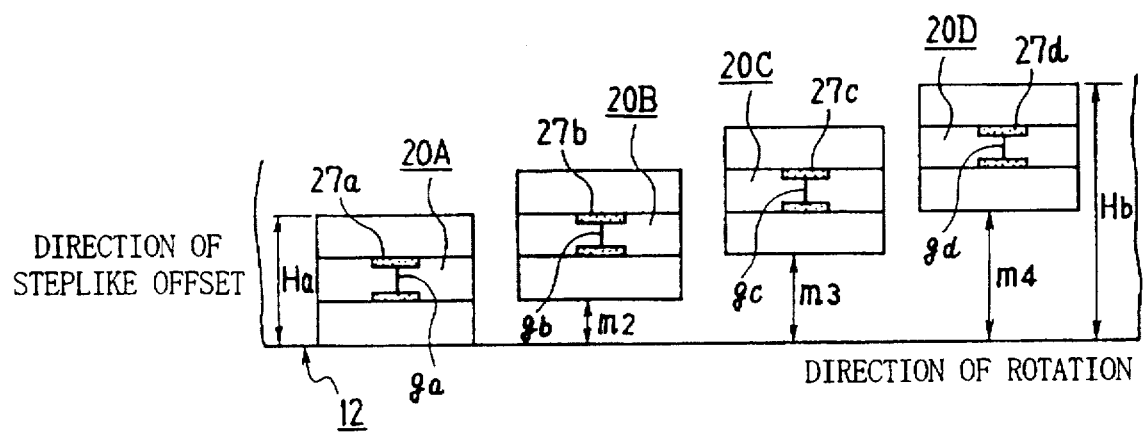
FIG. 8 is a view illustrating the magnetic heads shown in FIG. 7 in a developed form.

FIG. 7 is a conceptual view of a measuring apparatus 10 constructed in consideration of such a point. The illustrated example shows one in which four magnetic heads 20A through 20D are disposed with predetermined steplike offsets defined relative to each other in the direction of rotation of a drum. If the end surface of the drum is considered as the reference, the magnetic heads 20B, 20C and 20D identical in configuration to each other are disposed so as to have steplike offsets of m2, m3 and m4 with respect to the magnetic head 20A used as the reference as shown in FIG. 8. Symbols ga, gb, gc and gd respectively indicate gaps. Upper and lower ends of the gaps ga through gd are respectively filled with glass materials 27a through 27d as is already known.

Figure 9:
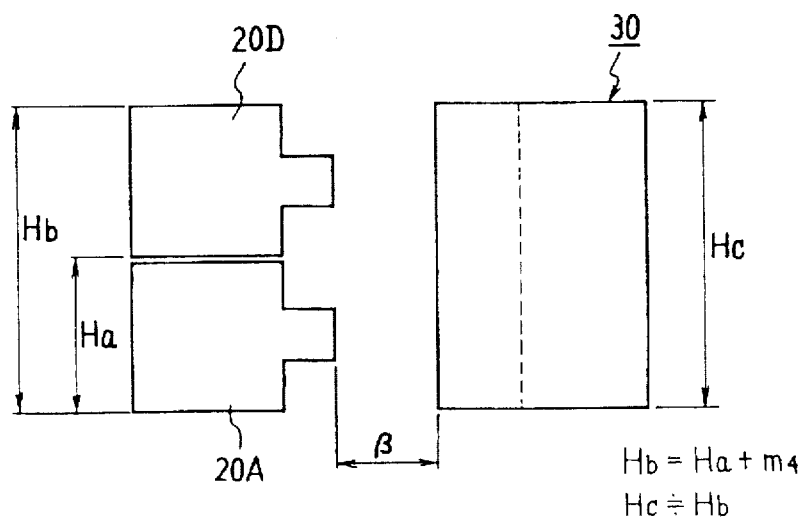
FIG. 9 is a layout as seen from the side of FIG. 7.

A magnetic sensor 30 disposed so as to be opposed to the plurality of magnetic heads 20 is constructed as shown in FIG. 9. If the thickness (extending in the axial direction of the rotating drum) of each magnetic head 20 is defined as Ha, a thickness Hb between the magnetic heads 20A and 20D is given by the following equation:

$$Hb=Ha+m4$$

Thus, a thickness Hc of the magnetic sensor 30 is given by the following expression so as to be able to cover all the magnetic heads 20:

$$Hc \geq Hb$$

If done so, the rates of wear of all the magnetic heads 20 can be measured by one magnetic sensor 30 alone. The above-described PG pulse is used to recognize whether the rates of wear of the magnetic heads 20 at any locations in space should be measured by the magnetic sensor 30. This is because the relationship in position between the timing provided to generate the PG pulse and each magnetic head is universally decided.

When the thickness of the magnetic sensor 30 is selected to the aforementioned value Hc, it is considered that the magnetic resistance Rc and Rd of the magnetic spaces differ from each other according to the magnetic heads 20A through 20D to be measured and hence the measuring accuracy varies. However, there is practically little difference. This is because the magnetic resistance of the core 31 itself is considered to be small.

Figure 10:
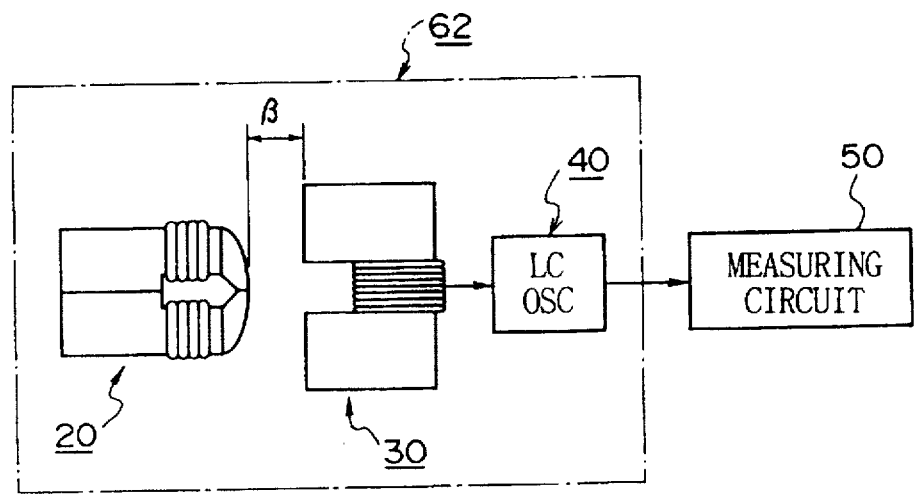
FIG. 10 is a view showing a device for measuring a variation in frequency due to a change in environmental temperature.

Since the above-described variable oscillator circuit 40 has a semiconductor element, the oscillating frequency thereof varies according to ambient environmental temperatures. A description of determining to which extent the oscillating frequency varies, will be made below. As shown in FIG. 10, the magnetic head 20, the magnetic sensor 30 and the variable oscillator circuit 40 are first accommodated within a thermostatic chamber 62. In this state, an internal temperature of the thermostatic chamber 62 is changed. When the internal temperature thereof is changed over a temperature range from $-5\_C$. to $45\_C$. at $10\_C$. intervals, oscillating frequencies at that time are represented in the form of a curve shown in FIG. 11.

Figure 11:
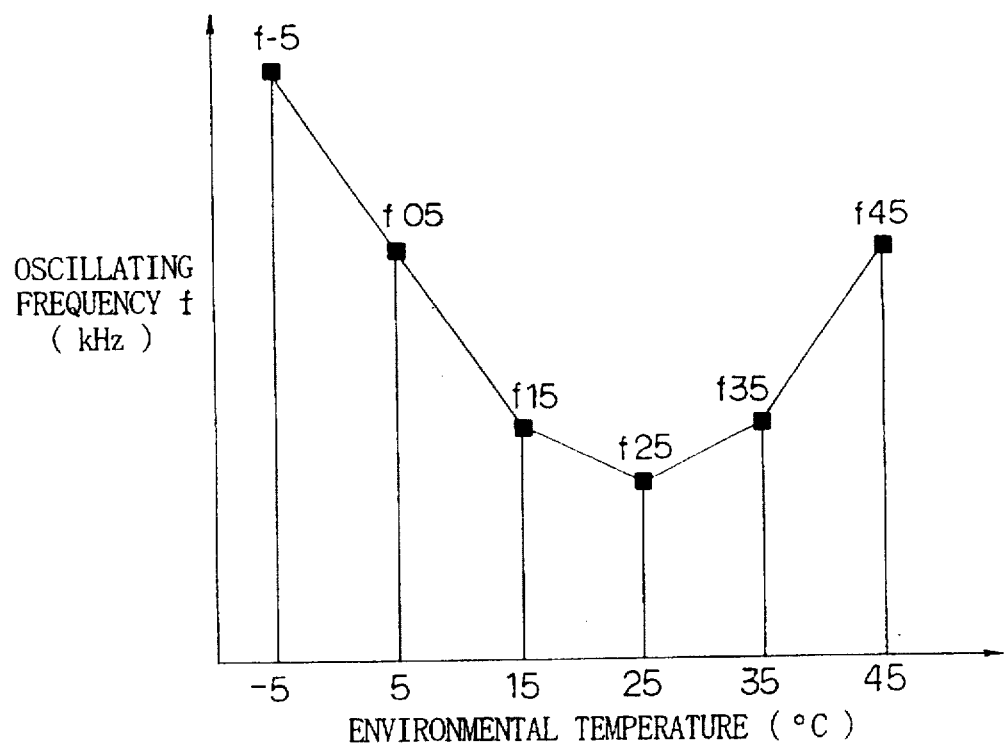
FIG. 11 is a characteristic diagram illustrating the relationship between the temperature and the oscillating frequency.

As is apparent from FIG. 11, such a parabola that the oscillating frequency f25 at ordinary temperatures (25° C.) is represented as the bottom, is plotted. Thus, when the oscillating frequency f also varies with a change in environmental temperature in this way, it is impossible to accurately measure the rate of wear. In the above-described AV device, the internal temperature of the device rises as the time becomes greater or increases from the turning on of a power supply. Therefore, there is a possibility that a large difference will occur in the result of calculation of the rate of wear upon turning on of the power supply and immediately before the turning off of the power supply. Accordingly, the measuring condition that, for example, the rate of wear is measured immediately after the turning on of the power supply, may be established or the compensation for temperature may preferably be performed. An example of the compensation for temperature will next be described.

Figure 12:
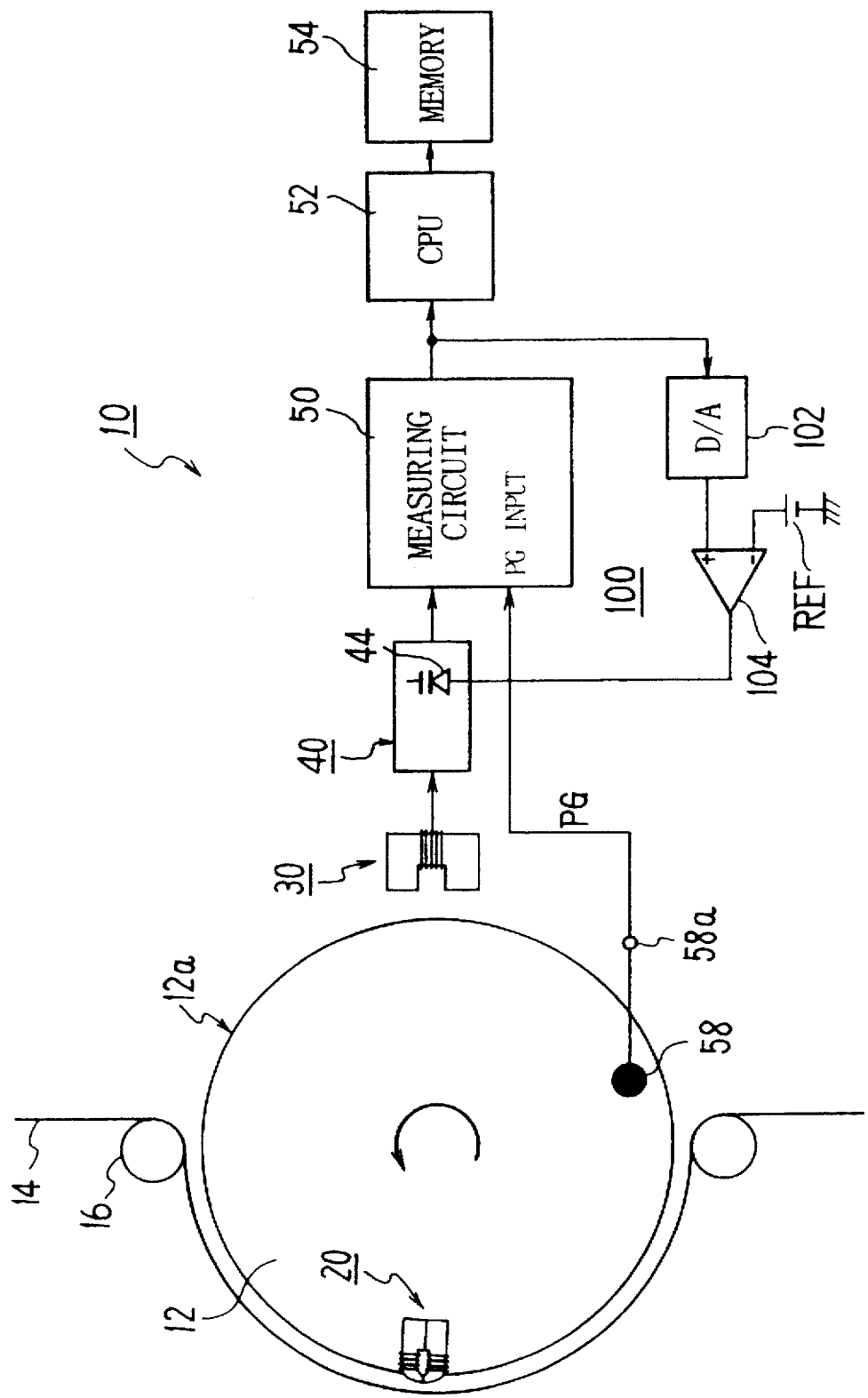
FIG. 12 is a fragmentary systematic diagram showing one example of a temperature compensated measuring apparatus.
Figure 13:
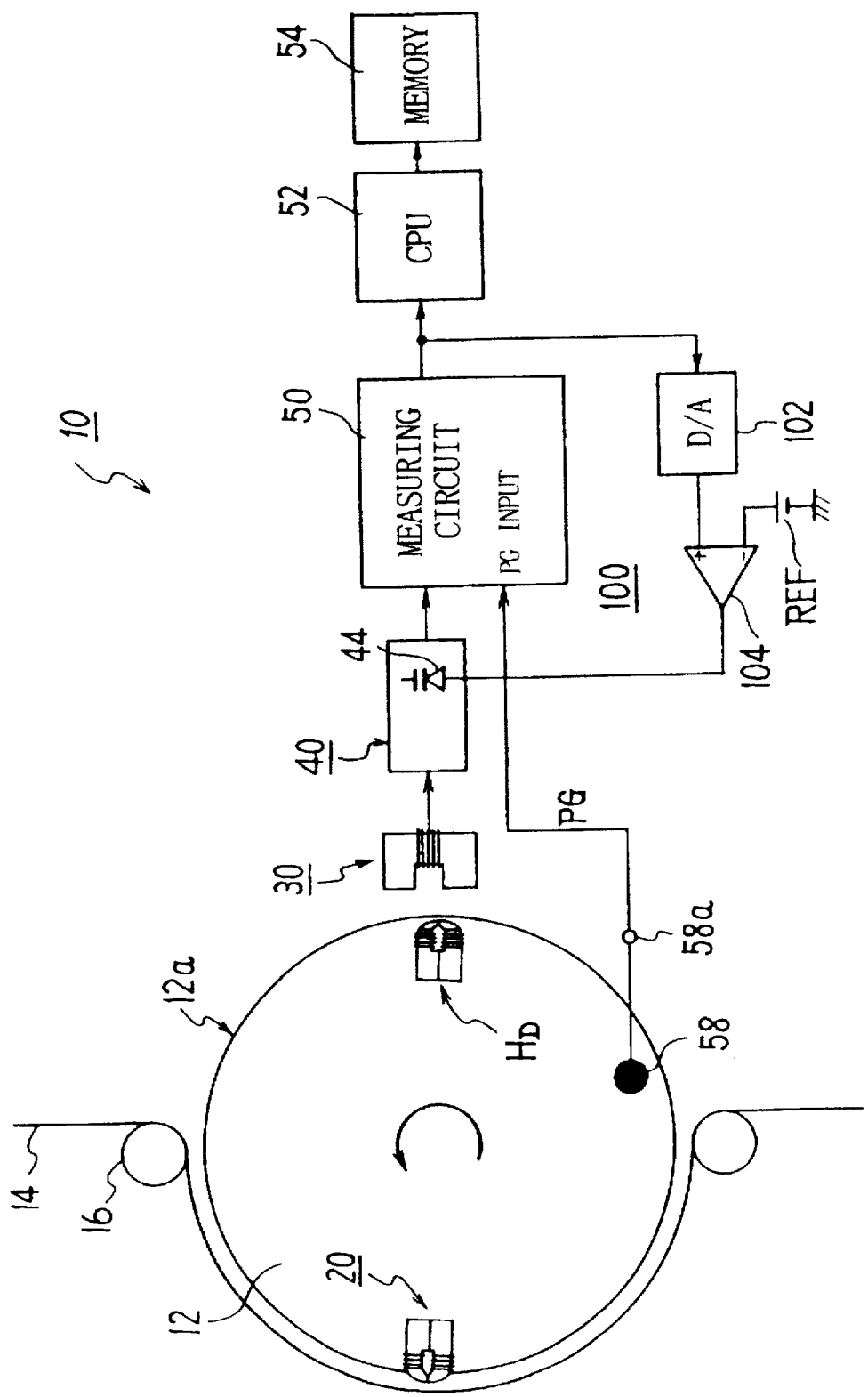
FIG. 13 is a fragmentary systematic diagram illustrating another example of the temperature compensated measuring apparatus.

FIGS. 12 and 13 respectively illustrate specific examples of temperature-compensated measuring apparatuses 10. The magnetic head 20 itself used for recording and playback cannot be used to calculate the oscillating frequency for temperature compensation. This is because the magnetic head 20 wears out with the time.

To cope with this, the example shown in FIG. 12 is provided which measures the oscillating frequency used for compensating for temperature when a drum surface 12a on which a magnetic head 20 is not provided, is opposed to a magnetic sensor 30.

Therefore, a temperature compensating means 100 is provided as illustrated in FIG. 12. A variable oscillator circuit 40 is also included in a loop of the temperature compensating means 100. The capacitive element 44 provided in the variable oscillator circuit 40 is replaced by a variable element. In the illustrated example, a variable capacity diode (varicap) is used as shown in FIG. 12.

A measuring circuit 50 is constructed as a digital measuring circuit. Measured data (digital data) corresponding to an oscillating frequency outputted from the measuring circuit 50 is supplied to a D/A converter 102 where it is converted into an analog level (e.g., voltage). This analog level is compared with a reference level REF by a level comparator 104. The reference level REF can be set to a value equivalent to an analog level at an oscillating frequency obtained at an ordinary temperature (25° C.).

A capacitive value of the variable capacity diode 44 is controlled by the compared output obtained from the level comparator 104 to maintain the oscillating frequency f25 at the ordinary temperature regardless of a variation in temperature. The temperature compensating operation may be done at intermittent intervals or continuously during a period in which the rate of wear of the head is being measured. It is apparent that whether the drum surface 12a with no magnetic head 20 provided thereon is in an opposing relationship to the magnetic sensor 30 can be judged from timing provided to output a PG pulse.

A dummy head HD different from the head for recording and reproduction can be also used in place of the use of the drum surface 12a with no magnetic head 20. FIG. 13 illustrates the example in which the dummy head HD is used. Thus, the degree of extension of the head is adjusted so that the dummy head HD used as for temperature compensation does not project from the peripheral surface of the drum. This is made to avoid the wearing away of the dummy head HD in use.

Further, a process for reading the value of the oscillating frequency obtained at the time that the dummy head HD faces the magnetic sensor 30 and performing feedback control so that the value thereof reaches the reference level REF is identical to that illustrated in FIG. 12. Rotating timing provided to oppose the dummy head HD to the magnetic sensor 30 is judged with the PG pulse as the reference. Since elements of structure other than the above are identical to those shown in FIG. 12, their description will be omitted.

Figure 14:
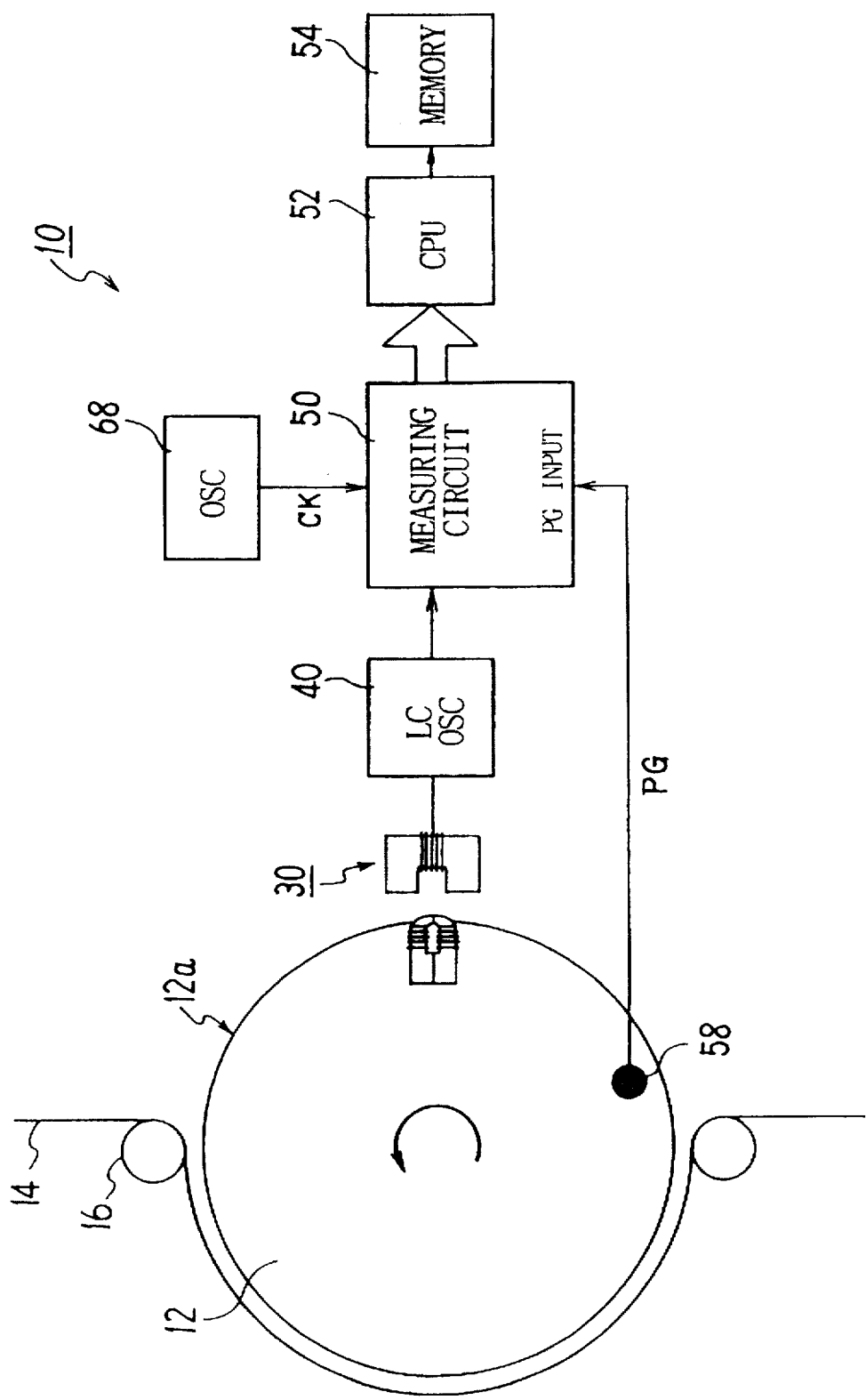
FIG. 14 is a conceptual view showing a digital type magnetic head wear-rate measuring apparatus.

The measuring apparatus 10 shown in FIG. 1 or 12 is suitable for use in a digital process. Its specific example will illustrated in FIG. 14 or later. FIG. 14 is a view showing the concept of the digital process. A measuring circuit 50 is constructed as a digital process system. Therefore, the measuring circuit 50 is provided with a reference clock source 68. The digital process is executed based on a reference train clock CK outputted from the reference clock source 68.

Figure 15:
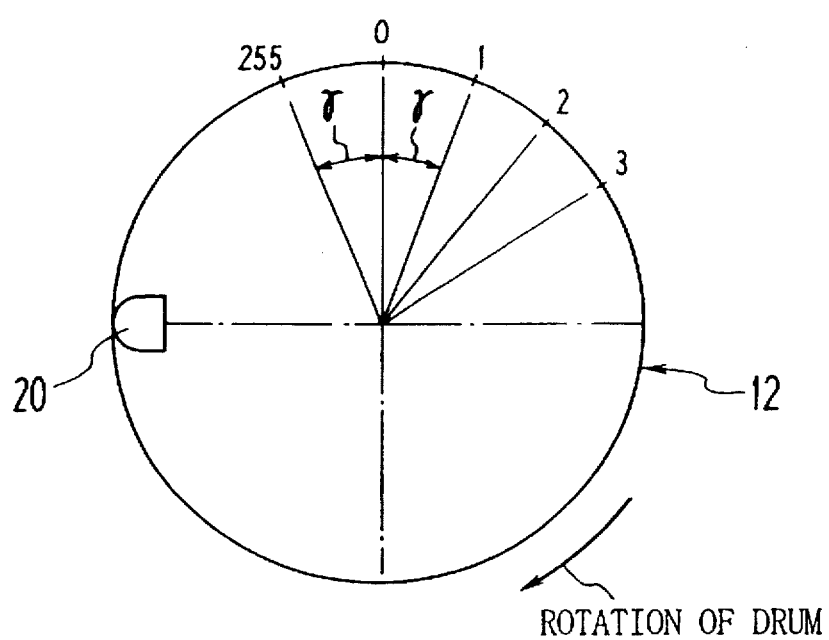
FIG. 15 is a view illustrating the relationship between measured angles with respect to one round of a drum.

When the digital process is executed, a region corresponding to one turn of a drum is divided into n and the rate of wear of a magnetic head 20 is calculated based on measured data in a divided region where the magnetic head 20 is actually positioned, of measured data obtained every n divisions. As shown in FIG. 15 by way of example, one turn of the drum is determined by being divided into 256 (2 to the eighth power).

Figure 16:
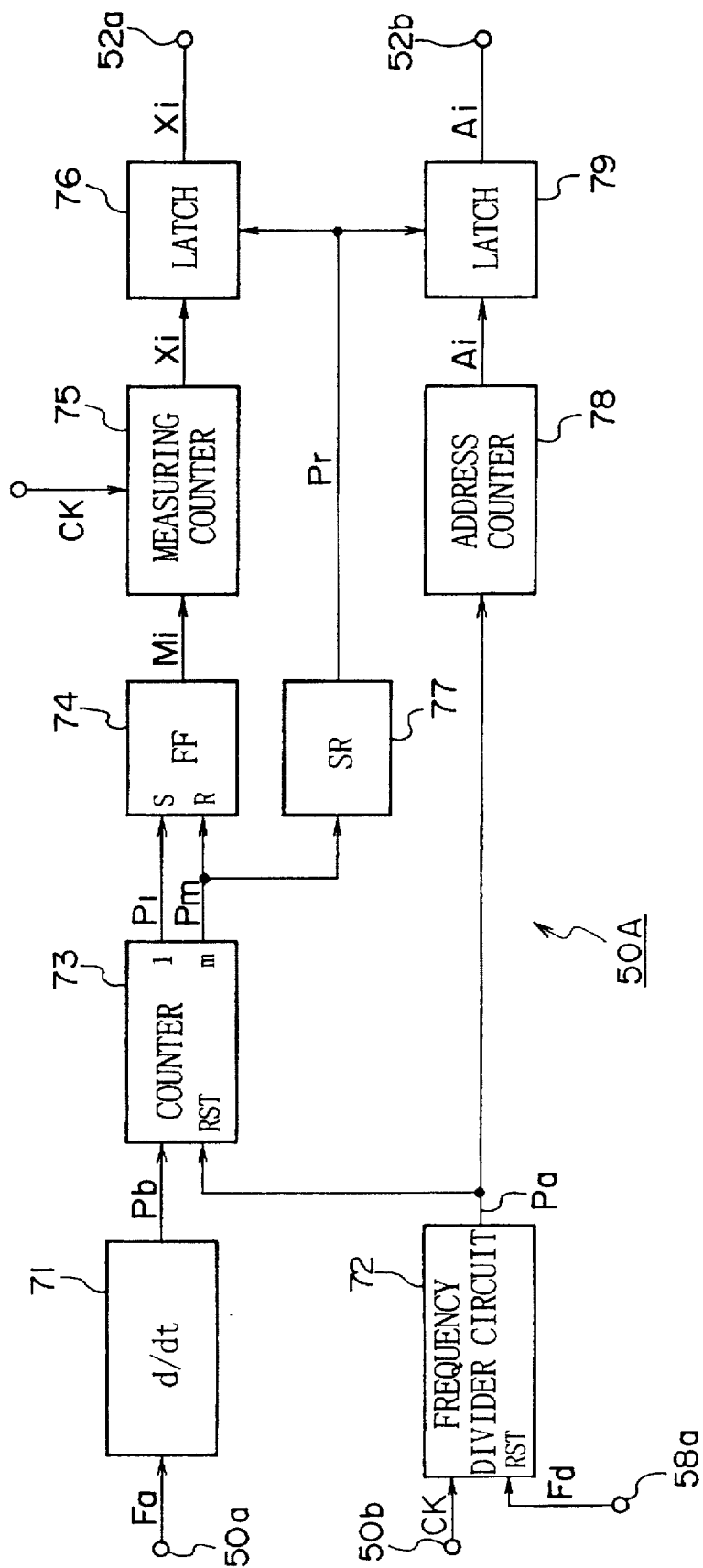
FIG. 16 is a systematic diagram showing one example of a measuring circuit employed in a noncontact type magnetic head wear-rate measuring apparatus.

FIG. 16 illustrates a specific example of the digital measuring circuit 50.

Figure 17:
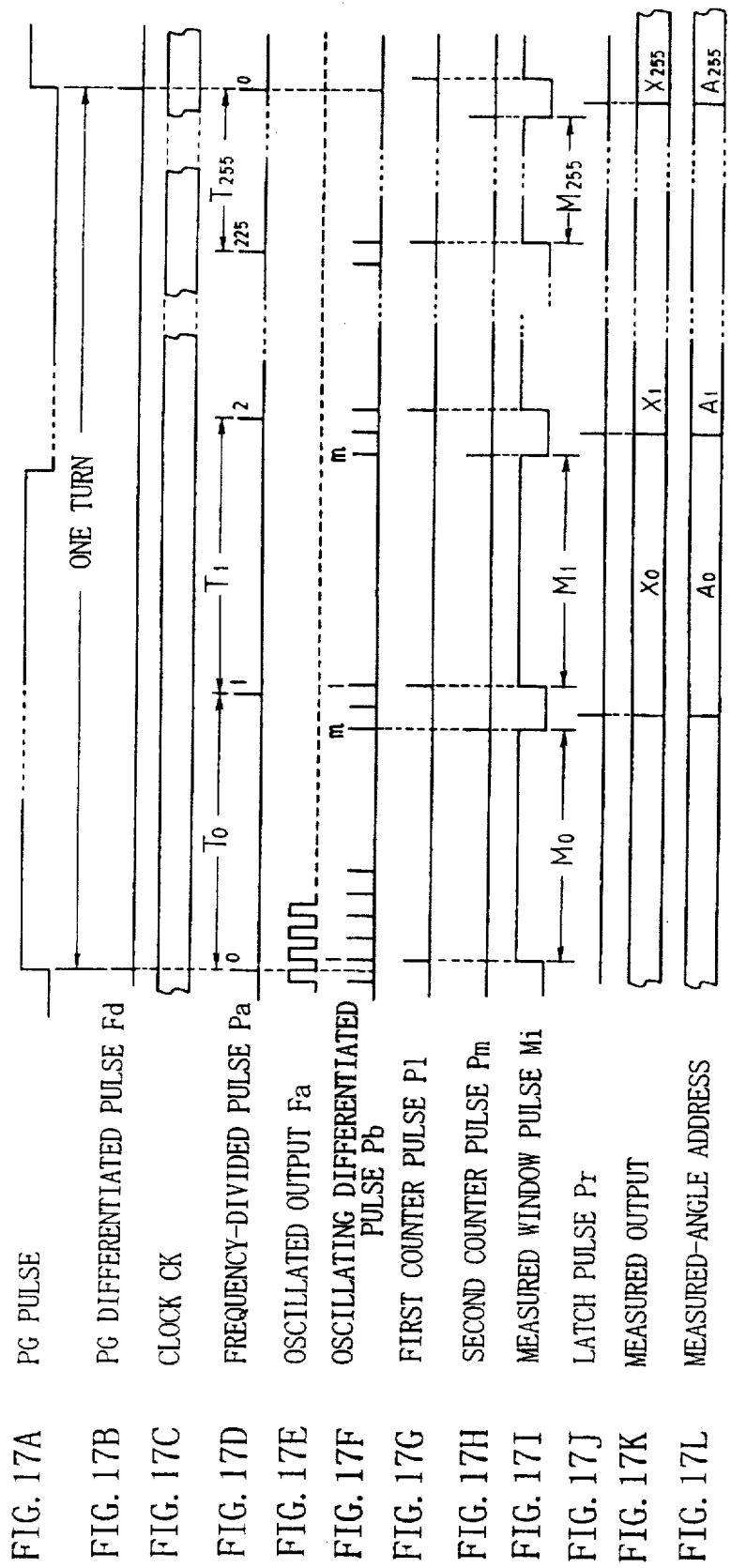
FIGS. 17A–17L are views for explaining the operation of the measuring circuit shown in FIG. 16.

An oscillated output (whose frequency: f25) Fa (see FIG. 17E) produced from a variable oscillator circuit 40 is supplied to a terminal 50a. A terminal 50b is supplied with a train clock CK (see FIG. 17C) sent from the reference clock source 68. Further, a terminal 58a is supplied with a pulse Fd (see FIG. 17B) obtained by differentiating one PG pulse (see FIG. 17A) outputted for each turn of the drum.

A frequency divider circuit 72 divides the clock CK by a division ratio for obtaining 256 pulses (frequency-divided pulses) for each turn of the drum. Since the frequency divider circuit 72 is supplied with the PG-differentiated pulse Fd as a reset pulse, a frequency-divided pulse Pa (see FIG. 17D) synchronized with the rotation of the drum is obtained from the frequency divider circuit 72.

The oscillated output Fa is differentiated by a differentiation circuit 71 and the resultant differentiated train pulse Pb (see FIG. 17F) is supplied to a counter 73. A first counter pulse P1 (see FIG. 17G) is outputted from the counter 73 with timing provided to input thereto a first pulse of the differentiated train pulse Pb input to the counter 73 from the differentiation circuit 71 after the reset of the counter 73. Further, a second counter pulse Pm (see FIG. 17H) is outputted from the counter 73 with timing provided to input an m-th pulse thereto. Since the frequency-divided pulse Pa has been supplied to the counter 73 as a reset pulse, the counter pulses P1 and Pm respectively serve as pulses each synchronized with the frequency-divided pulse Pa.

Since the counter pulses P1 and Pm are supplied as a set pulse and a reset pulse of a flip-flop circuit 74, a measured window train pulse Mi (see FIG. 17I) having a width equivalent to m pulses of the oscillated output Fa is obtained. This measured window train pulse Mi includes 256 pulses obtained per turn of the drum.

The measured window train pulse Mi is supplied to a measuring counter 75 and the number of clocks CK supplied to the counter 75 is counted by a width of each measured window pulse. Since the measured window pulses are different in width from each other according to the oscillating frequency, the value of an output Xi measured by the counter 75 also varies. The measured output Xi is latched in a latch circuit 76. Therefore, the second counter pulse Pm is supplied to a one-bit shift register 77 to generate a latch pulse Pr (see FIG. 17J) slightly time-delayed as compared with the second counter pulse Pm. Thus, a measured output Xi obtained after completion of the measurement is latched based on the latch pulse Pt. When the measured window pulse is M0, a measured output X0 is latched in the latch circuit 76. On the other hand, when the measured window pulse is M1, a measured output X1 is latched in the latch circuit 76 (see FIG. 17K).

In order to determine at which position (corresponding to a position of rotation of the drum at the time that the magnetic sensor 30 is used as the reference) the measured output Xi is outputted, the frequency-divided pulse Pa is supplied to an address counter 78 for pointing out the position (corresponding to a measured angular position) of rotation of the drum. When one turn of the drum is divided into 256, a 8-bit counter is used. A measured-angle address Ai obtained from the counter 78 is latched in a latch circuit 79 (see FIG. 17L). The same pulse Pr as described above is used as a latch pulse.

Thus, when the measured window pulse is M0, a measured-angle address A0 (00000000) and a measured output X0 are obtained at their corresponding output terminals 52a and 52b. When the measured window pulse is M255, for example, a measured-angle address A255 (11111111) and a measured output X255 at that time are obtained at their corresponding terminals 52a and 52b.

These measured data (corresponding to the measured-angle address Ai and measured output Xi) are supplied to a rate-of-wear calculating means 52 (CPU) shown in FIG. 14, where the degree of extension of the head from the drum surface is calculated based on measured data corresponding to a section or interval at which the magnetic head 20 is located. The rate of wear of the magnetic head 20 is predicted from the initial degree of head extension (stored in a memory 54) and the measured degree of head extension.

The relationship between the degree of head extension and the oscillating frequency is predicted by predetermining several positions of head extension as seen from the initial position of head extension and determining oscillating frequencies at the respective positions. The rate of wear of the head is calculated using the resultant predicted curve and the actually calculated degree of head extension.

Figure 18:
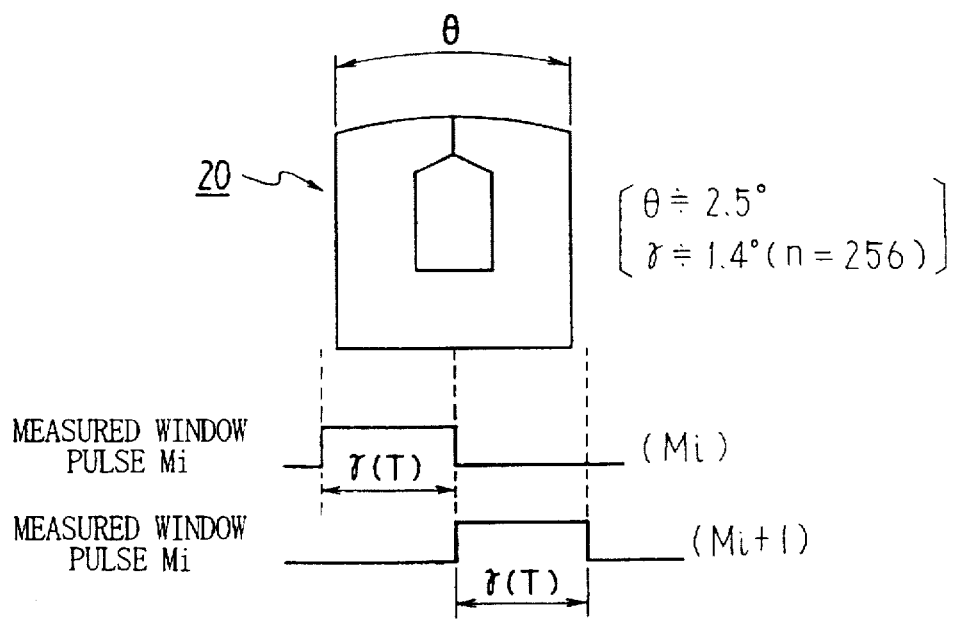
FIG. 18 is a view showing the relationship between a magnetic head and measured ranges.

When the width Wc of the magnetic head 20 is about 2.5 mm as described above, the width thereof is equivalent to about 2.5° as a result of conversion of the width thereof into the angle as shown in FIG. 18. When one turn of the drum is divided into 256, each measured angle γ becomes about 1.4°. Consequently, the degree of head extension is calculated from the measured output Xi derived from the two measured window pulses Mi.

However, this calculation illustrates a case when the timing provided for the end surface of the core of the magnetic head 20 and the timing for the measured window train pulse Mi coincide with each other. When the former timing differs from the latter timing, the degree of head extension is calculated based on at least three measured outputs Xi.

Figure 19:
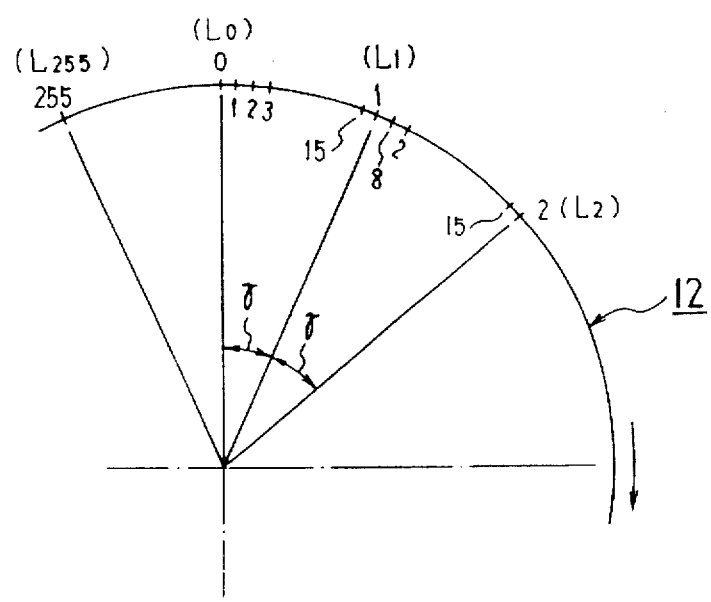
FIG. 19 is a view for describing high resolution for measurement.

It is clear that the calculation of the degree of head extension based on a number of measured outputs Xi provides a high-accuracy wear rate measurement. Namely, an improvement in measuring resolution is achieved. FIG. 19 and the subsequent drawings show examples each capable of improving measuring resolution and measuring the rate of wear of a head with high accuracy. According to the example to be described below, as shown in FIG. 19, one turn of the drum is divided into 256 and the divided respective one is further divided into 16. Thereafter, measured outputs Xi corresponding to 256×16 in total are determined and the rate of wear of the head is calculated from the measured outputs Xi.

As a method of dividing one turn of the drum into 256 and further dividing the divided respective one into 16, an example to be described later is known which utilizes a measurement cyclic pulse Ti corresponding to the 256 divisions. According to the present example, exactly 256×16 measured data can be obtained by successively shifting the measurement cyclic pulse Ti by ¹⁄₁₆ per turn of the drum and rotating the drum sixteen times.

Figure 20:
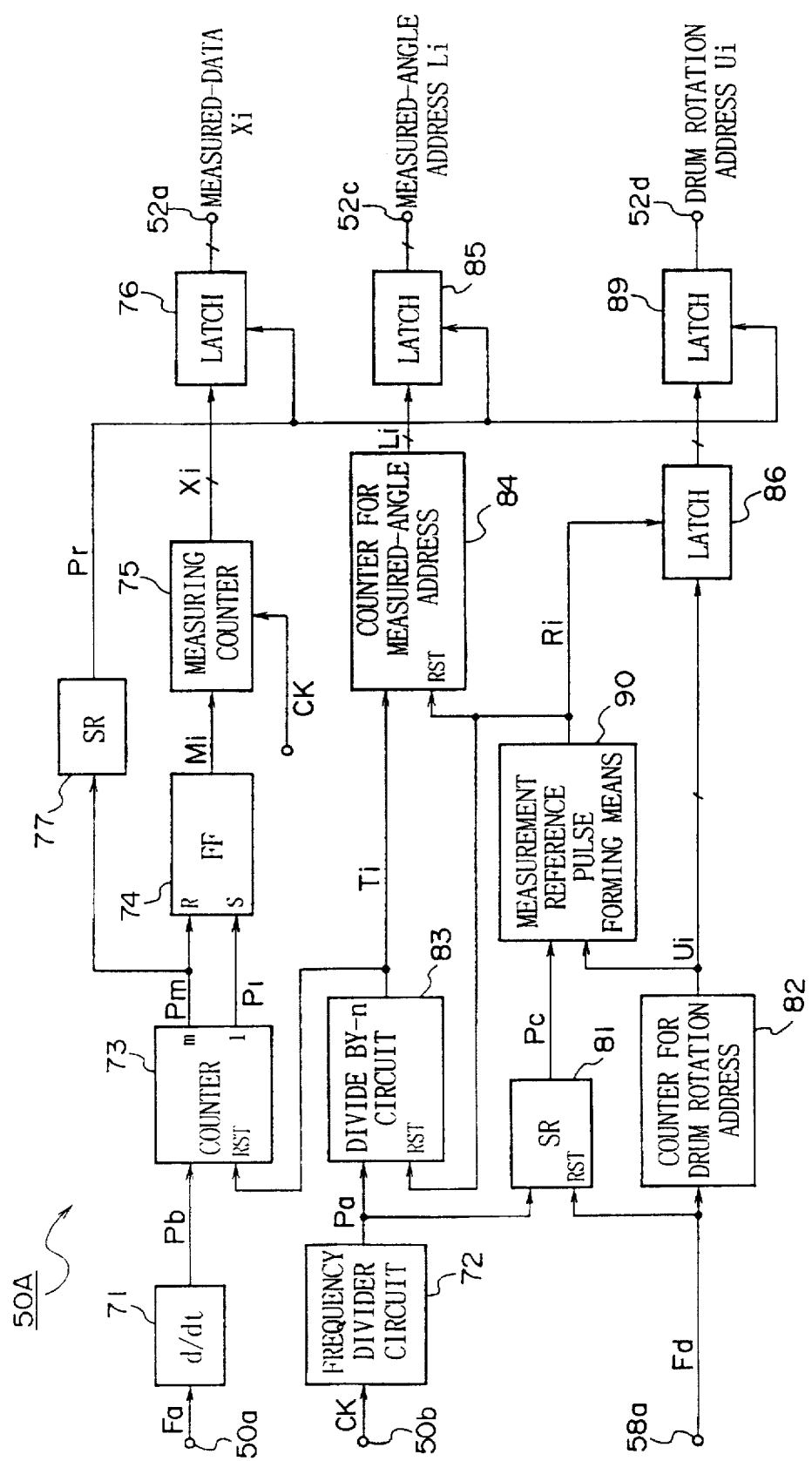
FIG. 20 is a systematic diagram showing one example of a digital measuring circuit for providing the high resolution for measurement.

FIG. 20 shows a specific example of a digital measuring circuit 50 for realizing the above-described process. A train clock CK supplied to a terminal 50b is supplied to a frequency divider circuit 72 to form a first frequency-divided pulse Pa (see FIG. 21B). The first frequency-divided pulse Pa is further supplied to a second frequency divider circuit 83 to form a measurement cyclic pulse Ti (see FIG. 21F) outputted by 256 pulses per turn of the drum.

An oscillated output Fa is supplied to a terminal 50a and differentiated by a differentiation circuit 71 to form an oscillating differentiated pulse Pb (see FIG. 21H). The oscillating differentiated pulse Pb is supplied to a counter 73 to generate first and second counter pulses P1 and Pm (see FIGS. 21I and 21J). Since the measurement cyclic pulse Ti is supplied to the counter 73 as a reset pulse, each of the counter pulses P1 and Pm is synchronized with the measurement cyclic pulse Ti.

The counter pulses P1 and Pm are supplied to a flip-flop circuit 74 provided in the subsequent stage to generate a measured window train pulse Mi shown in FIG. 21K. The train pulse Mi is generated in the form of 256 pulses. A measuring counter 75 counts the number of clocks CK supplied during an interval of each measured window pulse Mi and a measured output Xi (see FIG. 21L) corresponding to the count value of the counter 75 is latched in a latch circuit 76. A latch pulse generated from a shift register 77 for one-bit shifting is used as a latch pulse Pr shown in FIG. 21O.

On the other hand, a PG differentiated pulse Fd (see FIG. 21A) supplied to a terminal 58a is supplied to an address generating counter 82. As described above, the respective measured angles corresponding to the 256 divisions of one turn of the drum are respectively divided into 16. In this state, the rate of wear of the head is measured. However, the counter 82 is disposed to provide addresses corresponding to respective divided points at the time of the sixteen divisions and each synchronized with the rotation of the drum. Thus, the counter 82 is composed of a 4-bit counter. As shown in FIGS. 22A through 22C, the contents of data at a drum rotation address Ui are successively updated by 1 for each turn of the drum and the drum rotation address data Ui is returned to the original address data U0 after completion of sixteen turns.

The first frequency-divided pulse Pa is further supplied to a shift register 81 to generate a shift train pulse Pc corresponding to 16 pulses (see FIG. 21C). The shift pulse Pc is a phase shift pulse used to divide a unit measured angle into 16. Only sixteen pulses are outputted for each turn of the drum. The phase shift pulse Pc is obtained in synchronism with the PG differentiated pulse Fd and outputted with the same timing at all times.

As shown in FIG. 21C, the phase shift pulse Pc is 4-bit digital data, which is supplied to a measurement reference pulse forming means 90 together with the drum rotation address Ui.

Figure 23:
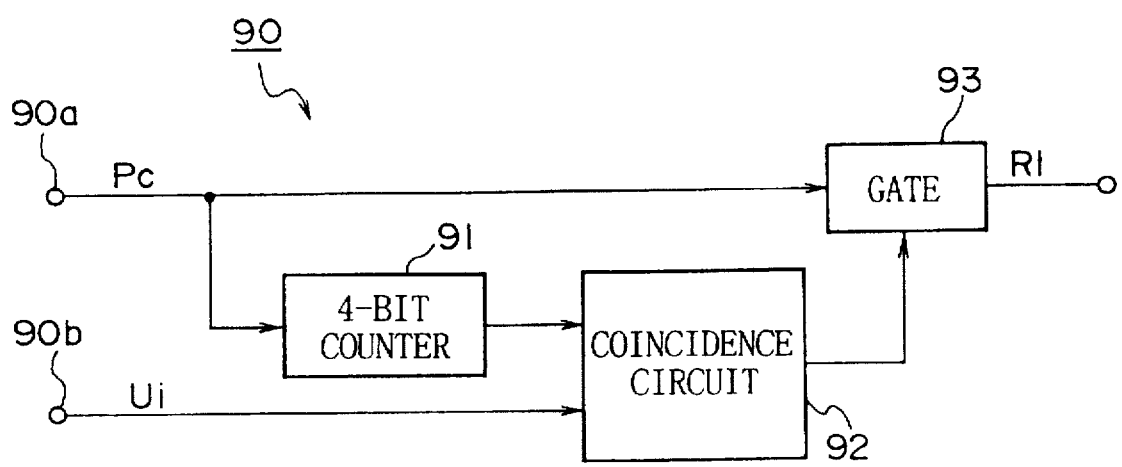
FIG. 23 is a systematic diagram illustrating a measurement reference pulse forming means.

FIG. 23 shows a specific example of the measurement reference pulse forming means 90. The phase shift pulse Pc is supplied to a 4-bit counter 91 through a terminal 90a. Digital data successively updated bit by bit is outputted from the 4-bit counter 91. A coincidence circuit 92 compares the digital data with the contents of data at the drum rotation address Ui supplied through a terminal 90b. Upon a first turn of the drum, as shown in FIGS. 21C and 21D by way of example, the drum rotation address Ui is represented as "0000" essively updated from the initial value "0000" of the phase shift pulse Pc for each pulse. Therefore, the contents of both data coincide with each other only when the phase shift pulse Pc at the first pulse is represented as "0000".

A gate circuit 93 is opened in response to the coincidence pulse so that the phase shift pulse Pc itself input thereto is outputted therefrom. Thus, when the drum rotation address Ui is represented as "0000" as shown in FIGS. 21C and 21D, a measurement reference pulse R0 (see FIG. 21E) is outputted with the initial pulse timing. Since the drum rotation address is represented as "0001" upon the second turn of the drum as shown in FIGS. 25C, 25D and 25E, a measurement reference pulse R1 is outputted with timing at which a phase shift pulse Pc "0001" corresponding to a second pulse is obtained. It is thus understood that the measurement reference pulse R1 at the second time is shifted by one pulse with respect to the measurement reference pulse R0 at the first time and is thereafter outputted. Accordingly, a position shifted by ¹⁄₁₆ becomes the position of the measurement reference pulse R1 if represented in the form of a measured angle γ.

Since the measurement reference pulse Ri is supplied to the frequency divider circuit 83 as the reset pulse as shown in FIG. 20, a frequency dividing operation is done after the measurement reference pulse Ri has been input to the frequency divider circuit 83. It is thus understood that the measurement cyclic pulse Ti is generated in synchronism with the measurement reference pulse Ri.

As a result, the measurement reference pulse Ri is generated in synchronism with a 0th phase shift pulse Pc in FIG. 21 (at the time of a first turn of the drum). The relationship between the measurement reference pulse Ri and the measured window pulse Mi is represented as shown in FIGS. 24A and 24E.

Referring similarly to FIG. 25 (at the time of a second turn of the drum), a measurement reference pulse Ri is generated in synchronism with a first phase shift pulse Pc. The relationship between the measurement reference pulse Ri and the measured window pulse Mi is given as FIGS. 24B and 24F. Since a measurement reference pulse R15 is generated in synchronism with a fifteenth phase shift pulse Pc upon a sixteenth turn of the drum, the relationship between FIGS. 24D and 24H is obtained.

Thus, since each position to be measured relative to the drum is gradually shifted even within a measuring angle γ by successively shifting the timing provided to generate the measurement reference pulse Ri, consequently, the measurement cyclic pulse Ti according to the rotation of the drum. Therefore, when the rotation of the drum reaches the sixteenth rotation, measured data Xi at respective positions obtained by dividing the measuring angle γ into sixteen equal angles are obtained.

A frequency-divided pulse Ti is supplied to a measured-angle address counter 84 to generate 256 addresses (measured-angle addresses) Li per turn of the drum. Since the counter 84 is reset by the measurement reference pulse Ri, the addresses are repeatedly generated for each turn of the drum. The measured-angle addresses Li are latched in a latch circuit 85. Using the measured-angle addresses Li, a decision about to which data at measured angles the present measured data Xi corresponds, is made.

The measurement reference pulse Ri is further supplied to a latch circuit 86 to latch the contents of a drum rotation address Ui therein. The contents thereof are further latched in a latch circuit 87 again in response to a latch pulse Pr. It is possible to judge, based on the drum rotation address Ui latched in the latch circuit 87, to which rotation the measured data corresponds. It is thus possible to reliably judge, based on the measured data Xi, drum rotation address Ui and measured-angle address Li obtained at terminals 52a, 52b and 52c, whether data at any of the measuring positions where one round or turn of the drum has been set to 256×16, is supplied to the rate-of-wear calculating means 52.

It is apparent that if the apparatuses each having the rotating magnetic head are used as described above, the present invention can be applied to all the head rate-of-wear measuring apparatuses.

In the noncontact type magnetic head rate-of-wear measuring apparatus according to the present invention, as has been described above, the magnetic sensor is disposed in a state of being in non-contact with the rotating magnetic head device. The degree of extension of the magnetic head from the drum surface, i.e., the rate of wear of the head can be measured by detecting the change in magnetic resistance of the magnetic circuit including the magnetic sensor.

According to the noncontact type magnetic head rate-of-wear measuring apparatus, it is possible to prevent a magnetic head to be measured from damage before it happens as compared with a contact type measuring apparatus using a contact or the like. Since the rate of wear of the head is measured according to a change in magnetic resistance unlike a noncontact type measuring apparatus using a laser beam or the like, measuring accuracy can be improved and the measuring apparatus itself can be reduced in size. Therefore, the measuring apparatus has a feature that allows it to be mounted to its mounting position without any restrictions. Thus, the measuring apparatus can be easily applied even to a rotating drum device whose drum diameter is small.

Since the rate of wear of the head can be detected by a single magnetic sensor disposed in an opposing relationship to a plurality of magnetic heads even when the plurality of magnetic heads are mounted to a rotating magnetic head device, measuring accuracy can be improved as compared with the case where a plurality of magnetic sensors are used. This is because it is unnecessary to make fine adjustment for allowing mounting positions of the respective magnetic sensors to be identical to each other. Further, since the number of the magnetic sensors disposed so as to be opposed to the drum surface is single, the scale of the measuring apparatus itself can be reduced. The measuring apparatus has an advantageous effect in terms of mounting, maintenance and inspections.

Since the compensation for temperature is done during measurement of the rate of wear of the head, a variation in measured data due to the temperature does not occur, so that the measuring accuracy is greatly improved. Since the measured data is processed in digital form, the measuring apparatus has an advantageous effect in that a circuit system can be reduced in size and improved in accuracy. Thus, the present invention is so suitable for use in AV devices such as a VTR, a DAT, a data recorder, etc.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. A noncontact type magnetic head wear-rate measuring apparatus, comprising;

a magnetic sensor opposed to a rotating magnetic head device with a magnetic head mounted thereon and disposed in noncontact with the rotating magnetic head device so as to fall outside an angle at which a magnetic tape is wound around the rotating magnetic head device; and rate-of-wear calculating means for calculating a rate of wear of the magnetic head in response to an output produced from said magnetic sensor, wherein said magnetic sensor is a part of a variable oscillator circuit and said rate-of-wear calculating means measures the rate of wear of the magnetic head according to a variation in oscillating frequency of said variable oscillator circuit at a position of rotation of said rotating magnetic head device where said magnetic sensor is opposed to said magnetic head.

2. The apparatus according to claim 1, wherein said rate-of-calculating means comprises:

means included in said variable oscillator circuit for deriving a variation in inductance due to a change in magnetic resistance of said magnetic sensor and outputting an oscillating frequency according to said variation;

a measuring circuit for outputting measured data proportional to the output of said variable oscillator circuit;

means for calculating the rate of wear of the magnetic head in response to the measured data output from said measuring circuit and producing calculated data; and a storage unit for storing said calculated data.

3. The apparatus according to claim 1, wherein said magnetic sensor is disposed at and fixed to a position in noncontact with said rotating magnetic head device.

4. The apparatus according to claim 1, wherein said magnetic sensor comprises an inverted U-shaped frame core and a detecting coil wound in a winding groove defined in the frame core.

5. The apparatus according to claim 4, wherein said winding groove has a width that is wider than a width of a gap of said magnetic head and narrower than a width of said magnetic head.

6. The apparatus according to claim 1, further including revolution detecting means provided on a direct extension of a radius which passes through the center of rotation of said rotating magnetic head device and wherein a position of rotation of said rotating magnetic head device opposed to said magnetic sensor is detected based on a rotational position reference signal outputted from said revolution detecting means.

7. The apparatus according to claim 1, wherein said rotating magnetic head device has a plurality of magnetic heads disposed so as to have predetermined steplike offsets relative to each other in a direction of rotation identical to said rotating magnetic head device, and said magnetic sensor has a height corresponding to a value larger than a sum of heights of said plurality of magnetic heads.

8. The apparatus according to claim 2, wherein said measuring circuit of said rate-of-wear calculating means is configured as a digital circuit and further includes temperature compensating means for receiving an output supplied from said measuring circuit and for comparing an output thereof with a reference oscillating frequency so that an oscillating frequency at an ordinary temperature is maintained regardless of a variation in temperature, to thereby control said rate-of-wear calculating means.

9. The apparatus according to claim 8, wherein said measuring circuit comprises a digital circuit add includes a frequency divider circuit for receiving a reference train clock and for frequency-dividing the received reference train clock by a predetermined division ratio;

a flip-flop for generating a measured window pulse having a width proportional to a pulse in the output of said variable oscillator circuit;

a measuring counter for counting a number of clocks in the reference clock train which are supplied within the measured window pulse; and an address counter for indicating the position of rotation of the rotating magnetic head device in response to a frequency-divided pulse supplied from said frequency divider circuit, wherein a region corresponding to one turn of the rotating magnetic head device is divided into n divisions and the rate of wear of said magnetic head is calculated based on output data in each division, said output data being obtained from said measuring circuit every n divisions.

* * * * *